US008506935B2

(12) United States Patent
Hale et al.

(10) Patent No.: US 8,506,935 B2

(45) Date of Patent: *Aug. 13, 2013

(54) RESPIRATORY DRUG CONDENSATION AEROSOLS AND METHODS OF MAKING AND USING THEM

(75) Inventors: Ron L. Hale, Sandia Park, NM (US); Peter M. Lloyd, Walnut Creek, CA (US); Amy T. Lu, Los Altos, CA (US); Joshua D. Rabinowitz, Princeton, NJ (US); Martin J. Wensley, Los Gatos, CA (US)

(73) Assignee: Alexza Pharmaceuticals, Inc., Mountain View, CA (US)

(*) Notice: Subject to any disclaimer, the term of this patent is extended or adjusted under 35 U.S.C. 154(b) by 134 days.

This patent is subject to a terminal disclaimer.

(21) Appl. No.: 12/490,102

(22) Filed: Jun. 23, 2009

(65) Prior Publication Data

US 2009/0258075 A1 Oct. 15, 2009

Related U.S. Application Data

(63) Continuation of application No. 10/719,899, filed on Nov. 20, 2003, now Pat. No. 7,550,133.

(60) Provisional application No. 60/429,364, filed on Nov. 26, 2002.

(51) Int. Cl.

| | |
|---|---|
| *A61K 9/12* | (2006.01) |
| *A61K 9/14* | (2006.01) |
| *A61M 15/00* | (2006.01) |
| *H05B 3/00* | (2006.01) |

(52) U.S. Cl.

USPC ............... 424/45; 424/46; 424/434; 424/489; 424/499; 514/958; 128/200.14; 128/200.24; 128/203.15

(58) Field of Classification Search

USPC ............. 424/45, 46, 434, 489, 499; 514/958; 128/200.14, 200.24, 203.15

See application file for complete search history.

(56) References Cited

U.S. PATENT DOCUMENTS

| | | | |
|---|---|---|---|
| 802,256 | A | 10/1905 | Bamberger et al. |
| 3,219,533 | A | 11/1965 | Mullins |
| 3,560,607 | A | 2/1971 | Hartley et al. |
| 3,949,743 | A | 4/1976 | Shanbrom |
| 3,982,095 | A | 9/1976 | Robinson |
| 4,141,369 | A | 2/1979 | Burruss |
| RE30,285 | E | 5/1980 | Babington |
| 4,474,191 | A | 10/1984 | Steiner |
| 4,484,576 | A | 11/1984 | Albarda |
| 4,566,451 | A | 1/1986 | Badewien |
| 4,708,151 | A | 11/1987 | Shelar |
| 4,734,560 | A | 3/1988 | Bowen |
| 4,735,217 | A | 4/1988 | Gerth et al. |
| 4,819,665 | A | 4/1989 | Roberts et al. |
| 4,848,374 | A | 7/1989 | Chard et al. |
| 4,853,517 | A | 8/1989 | Bowen et al. |
| 4,895,719 | A | 1/1990 | Radhakrishnun et al. |
| 4,906,417 | A | 3/1990 | Gentry |
| 4,917,119 | A | 4/1990 | Potter et al. |
| 4,924,883 | A | 5/1990 | Perfetti et al. |
| 4,941,483 | A | 7/1990 | Ridings et al. |
| 4,963,289 | A | 10/1990 | Ortiz et al. |
| 5,042,509 | A | 8/1991 | Banerjee et al. |
| 5,049,389 | A | 9/1991 | Radhakrishnun |
| 5,060,671 | A | 10/1991 | Counts et al. |
| 5,099,861 | A | 3/1992 | Clearman et al. |
| 5,135,009 | A | 8/1992 | Muller et al. |
| 5,144,962 | A | 9/1992 | Counts et al. |
| 5,146,915 | A | 9/1992 | Montgomery |
| 5,190,029 | A | 3/1993 | Byron et al. |
| 5,224,498 | A | 7/1993 | Deevi et al. |
| 5,345,951 | A | 9/1994 | Serrano et al. |
| 5,366,770 | A | 11/1994 | Wang |
| 5,388,574 | A | 2/1995 | Ingebrethsen |
| 5,456,247 | A | 10/1995 | Shilling et al. |
| 5,511,726 | A | 4/1996 | Greenspan et al. |
| 5,544,646 | A | 8/1996 | Lloyd et al. |

(Continued)

FOREIGN PATENT DOCUMENTS

| | | |
|---|---|---|
| CA | 2152684 | 1/1996 |
| EP | 0 358 114 | 3/1990 |

(Continued)

OTHER PUBLICATIONS

U.S. Appl. No. 11/687,466, filed Mar. 16, 2007, Zaffaroni et al.
U.S. Appl. No. 12/211,247, filed Sep. 16, 2008, Sharma et al.
U.S. Appl. No. 12/211,554, filed Sep. 16, 2008, Sharma et al.
U.S. Appl. No. 12/211,628, filed Sep. 16, 2008, Lei et al.
U.S. Appl. No. 12/352,582, filed Jan. 12, 2009, Hale et al.
U.S. Appl. No. 12/413,339, filed Mar. 27, 2009, Rabinowitz et al.
U.S. Appl. No. 12/471,070, filed May 22, 2009, Hale et al.
U.S. Appl. No. 12/474,680, filed May 29, 2009, Cross et al.
U.S. Appl. No. 12/485,704, filed Jun. 16, 2009, Damani et al.

(Continued)

*Primary Examiner* — Mina Haghighatian

(74) *Attorney, Agent, or Firm* — Swanson & Bratschun, L.L.C.

(57) ABSTRACT

Described herein are respiratory drug condensation aerosols and methods of making and using them. Kits for delivering condensation aerosols are also described. The respiratory drug aerosols typically comprise respiratory drug condensation aerosol particles. In some variations the respiratory drug compound is selected from the group consisting of β-adrenergics, methylxanthines, anticholinergics, corticosteroids, mediator-release inhibitors, anti-leukotriene drugs, asthma inhibitors, asthma antagonists, anti-endothelin drugs, prostacyclin drugs, ion channel or pump inhibitors, enhancers, or modulators and pharmaceutically acceptable analogs, derivatives, and mixtures thereof. Methods of treating a respiratory ailment using the described aerosols are also described. In general, the methods typically comprise the step of administering a therapeutically effective amount of respiratory drug condensation aerosol to a person with a respiratory ailment. Methods of forming a respiratory drug condensation aerosol are also described. The methods comprise the steps of vaporizing and condensing a respiratory drug composition.

14 Claims, 5 Drawing Sheets

(56) References Cited

U.S. PATENT DOCUMENTS

| | | | |
|---|---|---|---|
| 5,564,442 A | 10/1996 | MacDonald et al. | |
| 5,592,934 A | 1/1997 | Thwaites | |
| 5,605,146 A | 2/1997 | Sarela | |
| 5,649,554 A | 7/1997 | Sprinkel et al. | |
| 5,666,977 A | 9/1997 | Higgins et al. | |
| 5,694,919 A | 12/1997 | Rubsamen et al. | |
| 5,738,865 A | 4/1998 | Baichwal et al. | |
| 5,758,637 A | 6/1998 | Ivri et al. | |
| 5,819,756 A | 10/1998 | Mielordt | |
| 5,840,246 A | 11/1998 | Hammons et al. | |
| 5,855,913 A | 1/1999 | Hanes et al. | |
| 5,874,481 A | 2/1999 | Weers et al. | |
| 5,894,841 A | 4/1999 | Voges | |
| 5,918,595 A | 7/1999 | Olsson et al. | |
| 5,928,520 A | 7/1999 | Haumesser | |
| 5,934,272 A | 8/1999 | Lloyd et al. | |
| 5,957,124 A | 9/1999 | Lloyd et al. | |
| 5,960,792 A | 10/1999 | Lloyd et al. | |
| 5,993,805 A | 11/1999 | Sutton et al. | |
| 6,041,777 A | 3/2000 | Faithfull et al. | |
| 6,051,566 A | 4/2000 | Bianco | |
| 6,090,212 A | 7/2000 | Mahawili | |
| 6,095,134 A | 8/2000 | Sievers et al. | |
| 6,095,153 A | 8/2000 | Kessler et al. | |
| 6,102,036 A | 8/2000 | Slutsky et al. | |
| 6,131,570 A | 10/2000 | Schuster et al. | |
| 6,234,167 B1 | 5/2001 | Cox et al. | |
| 6,241,969 B1 | 6/2001 | Saidi et al. | |
| 6,255,334 B1 | 7/2001 | Sands | |
| 6,506,762 B1 | 1/2003 | Horvath et al. | |
| 6,514,482 B1 | 2/2003 | Bartus et al. | |
| 6,591,839 B2 | 7/2003 | Meyer et al. | |
| 6,632,047 B2 | 10/2003 | Vinegar et al. | |
| 6,682,716 B2 | 1/2004 | Hodges et al. | |
| 6,701,922 B2 | 3/2004 | Hindle et al. | |
| 6,716,415 B2 | 4/2004 | Rabinowitz et al. | |
| 6,716,416 B2 | 4/2004 | Rabinowitz et al. | |
| 6,716,417 B2 | 4/2004 | Rabinowitz et al. | |
| 6,737,042 B2 | 5/2004 | Rabinowitz et al. | |
| 6,737,043 B2 | 5/2004 | Rabinowitz et al. | |
| 6,740,307 B2 | 5/2004 | Rabinowitz et al. | |
| 6,740,308 B2 | 5/2004 | Rabinowitz et al. | |
| 6,740,309 B2 | 5/2004 | Rabinowitz et al. | |
| 6,743,415 B2 | 6/2004 | Rabinowitz et al. | |
| 6,759,029 B2 | 7/2004 | Hale et al. | |
| 6,772,756 B2 | 8/2004 | Shayan | |
| 6,776,978 B2 | 8/2004 | Rabinowitz et al. | |
| 6,780,399 B2 | 8/2004 | Rabinowitz et al. | |
| 6,780,400 B2 | 8/2004 | Rabinowitz et al. | |
| 6,783,753 B2 | 8/2004 | Rabinowitz et al. | |
| 6,797,259 B2 | 9/2004 | Rabinowitz et al. | |
| 6,803,031 B2 | 10/2004 | Rabinowitz et al. | |
| 6,805,853 B2 | 10/2004 | Rabinowitz et al. | |
| 6,805,854 B2 | 10/2004 | Hale et al. | |
| 6,814,954 B2 | 11/2004 | Rabinowitz et al. | |
| 6,814,955 B2 | 11/2004 | Rabinowitz et al. | |
| 6,855,310 B2 | 2/2005 | Rabinowitz et al. | |
| 6,884,408 B2 | 4/2005 | Rabinowitz et al. | |
| 6,994,843 B2 | 2/2006 | Rabinowitz et al. | |
| 7,005,121 B2 | 2/2006 | Rabinowitz et al. | |
| 7,005,122 B2 | 2/2006 | Hale et al. | |
| 7,008,615 B2 | 3/2006 | Rabinowitz et al. | |
| 7,008,616 B2 | 3/2006 | Rabinowitz et al. | |
| 7,011,819 B2 | 3/2006 | Hale et al. | |
| 7,011,820 B2 | 3/2006 | Rabinowitz et al. | |
| 7,014,840 B2 | 3/2006 | Hale et al. | |
| 7,014,841 B2 | 3/2006 | Rabinowitz et al. | |
| 7,018,619 B2 | 3/2006 | Rabinowitz et al. | |
| 7,018,620 B2 | 3/2006 | Rabinowitz et al. | |
| 7,018,621 B2 | 3/2006 | Hale et al. | |
| 7,022,312 B2 | 4/2006 | Rabinowitz et al. | |
| 7,029,658 B2 | 4/2006 | Rabinowitz et al. | |
| 7,033,575 B2 | 4/2006 | Rabinowitz et al. | |
| 7,045,118 B2 | 5/2006 | Rabinowitz et al. | |
| 7,045,119 B2 | 5/2006 | Rabinowitz et al. | |
| 7,048,909 B2 | 5/2006 | Rabinowitz et al. | |
| 7,052,679 B2 | 5/2006 | Rabinowitz et al. | |
| 7,052,680 B2 | 5/2006 | Rabinowitz et al. | |
| 7,060,254 B2 * | 6/2006 | Rabinowitz et al. | 424/45 |
| 7,060,255 B2 | 6/2006 | Rabinowitz et al. | |
| 7,063,830 B2 | 6/2006 | Rabinowitz et al. | |
| 7,063,831 B2 | 6/2006 | Rabinowitz et al. | |
| 7,063,832 B2 | 6/2006 | Rabinowitz et al. | |
| 7,067,114 B2 | 6/2006 | Rabinowitz et al. | |
| 7,070,761 B2 | 7/2006 | Rabinowitz et al. | |
| 7,070,762 B2 | 7/2006 | Rabinowitz et al. | |
| 7,070,763 B2 | 7/2006 | Rabinowitz et al. | |
| 7,070,764 B2 | 7/2006 | Rabinowitz et al. | |
| 7,070,765 B2 | 7/2006 | Rabinowitz et al. | |
| 7,070,766 B2 | 7/2006 | Rabinowitz et al. | |
| 7,078,016 B2 | 7/2006 | Rabinowitz et al. | |
| 7,078,017 B2 | 7/2006 | Rabinowitz et al. | |
| 7,078,018 B2 | 7/2006 | Rabinowitz et al. | |
| 7,078,019 B2 | 7/2006 | Rabinowitz et al. | |
| 7,078,020 B2 | 7/2006 | Rabinowitz et al. | |
| 7,087,216 B2 | 8/2006 | Rabinowitz et al. | |
| 7,087,217 B2 | 8/2006 | Rabinowitz et al. | |
| 7,087,218 B2 | 8/2006 | Rabinowitz et al. | |
| 7,090,830 B2 | 8/2006 | Hale et al. | |
| 7,094,392 B2 | 8/2006 | Rabinowitz et al. | |
| 7,108,847 B2 | 9/2006 | Rabinowitz et al. | |
| 7,115,250 B2 | 10/2006 | Rabinowitz et al. | |
| 7,169,378 B2 | 1/2007 | Rabinowitz et al. | |
| 7,402,777 B2 | 7/2008 | Ron et al. | |
| 7,442,368 B2 | 10/2008 | Rabinowitz et al. | |
| 7,445,768 B2 | 11/2008 | Rabinowitz et al. | |
| 7,449,172 B2 | 11/2008 | Rabinowitz et al. | |
| 7,449,173 B2 | 11/2008 | Rabinowitz et al. | |
| 7,449,174 B2 | 11/2008 | Rabinowitz et al. | |
| 7,449,175 B2 | 11/2008 | Rabinowitz et al. | |
| 7,458,374 B2 | 12/2008 | Hale et al. | |
| 7,465,435 B2 | 12/2008 | Rabinowitz et al. | |
| 7,465,436 B2 | 12/2008 | Rabinowitz et al. | |
| 7,465,437 B2 | 12/2008 | Rabinowitz et al. | |
| 7,468,179 B2 | 12/2008 | Rabinowitz et al. | |
| 7,470,421 B2 | 12/2008 | Rabinowitz et al. | |
| 7,485,285 B2 | 2/2009 | Rabinowitz et al. | |
| 7,488,469 B2 | 2/2009 | Rabinowitz et al. | |
| 7,491,047 B2 | 2/2009 | Rabinowitz et al. | |
| 7,498,019 B2 | 3/2009 | Hale et al. | |
| 7,507,397 B2 | 3/2009 | Rabinowitz et al. | |
| 7,507,398 B2 | 3/2009 | Rabinowitz et al. | |
| 7,510,702 B2 | 3/2009 | Rabinowitz et al. | |
| 7,524,484 B2 | 4/2009 | Rabinowitz et al. | |
| 7,537,009 B2 | 5/2009 | Hale et al. | |
| 7,540,286 B2 | 6/2009 | Cross et al. | |
| 7,550,133 B2 | 6/2009 | Hale et al. | |
| 7,585,493 B2 * | 9/2009 | Hale et al. | 424/45 |
| 7,601,337 B2 * | 10/2009 | Rabinowitz et al. | 424/45 |
| 7,645,442 B2 * | 1/2010 | Hale et al. | 424/45 |
| 7,766,013 B2 * | 8/2010 | Wensley et al. | 128/203.27 |
| 2001/0020147 A1 | 9/2001 | Staniforth et al. | |
| 2001/0039262 A1 | 11/2001 | Venkataraman | |
| 2002/0037828 A1 | 3/2002 | Wilson et al. | |
| 2002/0058009 A1 | 5/2002 | Bartus et al. | |
| 2002/0086852 A1 | 7/2002 | Cantor | |
| 2002/0112723 A1 | 8/2002 | Schuster et al. | |
| 2002/0176841 A1 | 11/2002 | Barker et al. | |
| 2003/0004142 A1 | 1/2003 | Prior et al. | |
| 2003/0015196 A1 | 1/2003 | Hodges et al. | |
| 2003/0032638 A1 | 2/2003 | Kim et al. | |
| 2003/0051728 A1 | 3/2003 | Lloyd et al. | |
| 2003/0062042 A1 | 4/2003 | Wensley et al. | |
| 2003/0118512 A1 | 6/2003 | Shen | |
| 2003/0131843 A1 | 7/2003 | Lu | |
| 2003/0138508 A1 | 7/2003 | Novack et al. | |
| 2004/0009128 A1 | 1/2004 | Rabinowitz et al. | |
| 2004/0096402 A1 | 5/2004 | Hodges et al. | |
| 2004/0099266 A1 | 5/2004 | Cross et al. | |
| 2004/0101481 A1 | 5/2004 | Hale et al. | |
| 2004/0102434 A1 | 5/2004 | Hale et al. | |
| 2004/0105818 A1 | 6/2004 | Every et al. | |
| 2004/0234699 A1 | 11/2004 | Hale et al. | |
| 2004/0234914 A1 | 11/2004 | Hale et al. | |

| | | | |
|---|---|---|---|
| 2004/0234916 | A1 | 11/2004 | Hale et al. |
| 2005/0034723 | A1 | 2/2005 | Bennett et al. |
| 2005/0037506 | A1 | 2/2005 | Hale et al. |
| 2005/0079166 | A1 | 4/2005 | Damani et al. |
| 2005/0126562 | A1 | 6/2005 | Rabinowitz et al. |
| 2005/0131739 | A1 | 6/2005 | Rabinowitz et al. |
| 2005/0268911 | A1 | 12/2005 | Cross et al. |
| 2006/0032496 | A1 | 2/2006 | Hale et al. |
| 2006/0032501 | A1 | 2/2006 | Hale et al. |
| 2006/0120962 | A1 | 6/2006 | Rabinowitz et al. |
| 2006/0193788 | A1 | 8/2006 | Hale et al. |
| 2006/0257329 | A1 | 11/2006 | Rabinowitz et al. |
| 2006/0280692 | A1 | 12/2006 | Rabinowitz et al. |
| 2007/0028916 | A1 | 2/2007 | Hale et al. |
| 2007/0031340 | A1 | 2/2007 | Hale et al. |
| 2007/0122353 | A1 | 5/2007 | Hale et al. |
| 2007/0140982 | A1 | 6/2007 | Every et al. |
| 2007/0286816 | A1 | 12/2007 | Hale et al. |
| 2008/0110872 | A1 | 5/2008 | Hale et al. |
| 2008/0175796 | A1 | 7/2008 | Rabinowitz et al. |
| 2008/0216828 | A1 | 9/2008 | Wensley |
| 2008/0299048 | A1 | 12/2008 | Hale et al. |
| 2008/0306285 | A1 | 12/2008 | Hale et al. |
| 2008/0311176 | A1 | 12/2008 | Hale et al. |
| 2009/0062254 | A1 | 3/2009 | Hale et al. |
| 2009/0071477 | A1 | 3/2009 | Hale et al. |

FOREIGN PATENT DOCUMENTS

| | | |
|---|---|---|
| EP | 0 606 486 | 7/1994 |
| EP | 1 080 720 | 3/2001 |
| GB | 502 761 | 1/1938 |
| WO | WO 90/02737 | 3/1990 |
| WO | WO 94/09842 | 5/1994 |
| WO | WO 96/09846 | 4/1996 |
| WO | WO 96/13161 | 5/1996 |
| WO | WO 96/13290 | 5/1996 |
| WO | WO 96/13291 | 5/1996 |
| WO | WO 96/13292 | 5/1996 |
| WO | WO 96/30068 | 10/1996 |
| WO | WO 97/27804 | 8/1997 |
| WO | WO 97/36574 | 10/1997 |
| WO | WO 98/22170 | 5/1998 |
| WO | WO 98/31346 | 7/1998 |
| WO | WO 98/36651 | 8/1998 |
| WO | WO 99/16419 | 4/1999 |
| WO | WO 99/64094 | 12/1999 |
| WO | WO 00/00176 | 1/2000 |
| WO | WO 00/00215 | 1/2000 |
| WO | WO 00/27363 | 5/2000 |
| WO | WO 00/29053 | 5/2000 |
| WO | WO 00/47203 | 9/2000 |
| WO | WO 00/64940 | 11/2000 |
| WO | WO 00/66084 | 11/2000 |
| WO | WO 00/66206 | 11/2000 |
| WO | WO 00/76673 | 12/2000 |
| WO | WO 01/05459 | 1/2001 |
| WO | WO 02/24158 | 3/2002 |
| WO | WO 03/37412 | 5/2003 |

OTHER PUBLICATIONS

Bennett, R. L. et al. (1981). "Patient-Controlled Analgesia: A New Concept of Postoperative Pain Relief," Annual Surg. 195(6):700-705.

Carroll, M.E. et al. (1990), "Cocaine-Base Smoking in Rhesus Monkey: Reinforcing and Physiological Effects," Psychopharmacology (Berl) 102:443-450.

Clark, A. and Byron, P. (1986). "Dependence of Pulmonary Absorption Kinetics on Aerosol Particle Size," Z. Erkrank. 166:13-24.

Darquenne, C. et al. (1997). "Aerosol Dispersion in Human Lung: Comparison Between Numerical Simulations and Experiments for Bolus Tests," American Physiological Society. 966-974.

Davies, C. N. et al. (May 1972). "Breathing of Half-Micron Aerosols," Journal of Applied Physiology. 32(5):591-600.

Dershwitz, M., M.D., et al. (Sep. 2000). "Pharmacokinetics and Pharmacodynamics of Inhaled versus Intravenous Morphine in Healthy Volunteers," Anesthesiology. 93(3): 619-628.

Finlay, W. H. (2001). "The Mechanics of Inhaled Pharmaceutical Aerosols", Academic Press: San Diego Formula 2.39. pp. 3-14 (Table of Contents). pp. v-viii.

Gonda, I. (1991). "Particle Deposition in the Human Respiratory Tract," Chapter 176, The Lung: Scientific Foundations. Crystal R.G. and West, J.B. (eds.), Raven Publishers, New York. pp. 2289-2294.

Hatsukami D., et al. (May 1990) "A Method for Delivery of Precise Doses of Smoked Cocaine-Base to Human." Pharmacology Biochemistry & Behavior. 36(1):1-7.

Heyder, J. et al. (1986). "Deposition of Particles in the Human Respiratory Tract in the Size Range 0.005-15 μm," J. Aerosol Sci. 17(5):811-822.

Huizer, H. (1987). "Analytical Studies on Illicit Heron. V. Efficacy of Volitization During Heroin Smoking." Pharmaceutisch Weekblad Scientific Edition. 9(4):203-211.

Hurt, R. D., MD and Robertson, C. R., PhD, (Oct. 1998). "Prying Open the Door to the Tobacco Industry's Secrets About Nicotine: The Minnesota Tobacco Trial," JAMA 280(13):1173-1181.

Lichtman, A. H. et al. (1996). "Inhalation Exposure to Volatilized Opioids Produces Antinociception in Mice," Journal of Pharmacology and Experimental Therapeutics. 279(1):69-76 XP-001118649.

Martin, B. R. and Lue, L. P. (May/Jun. 1989). "Pyrolysis and Volatilization of Cocaine," Journal of Analytical Toxicology 13:158-162.

Mattox, A.J. and Carroll, M.E. (1996). "Smoked Heroin Self-Administration in Rhesus Monkeys," Psychopharmacology 125:195-201.

Meng, Y. et al. (1997). "Inhalation Studies with Drugs of Abuse", NIDA Research Monogragh 173:201-224.

Meng, Y., et al. (1999). "Pharmacological effects of methamphetamine and other stimulants via inhalation exposure," Drug and Alcohol Dependence. 53:111-120.

Pankow, J. (Mar. 2000). ACS Conference-San Francisco-Mar. 26, 2000. Chemistry of Tobacco Smoke. pp. 1-8.

Pankow, J. F. et al. (1997). "Conversion of Nicotine in Tobacco Smoke to Its Volatile and Available Free-Base Form through the Action of Gaseous Ammonia," Environ. Sci. Technol. 31:2428-2433.

Seeman, J. et al. (1999). "The Form of Nicotine in Tobacco. Thermal Transfer of Nicotine and Nicotine Acid Salts to Nicotine in the Gas Phase," J. Agric. Food Chem. 47(12):5133-5145.

Sekine, H. and Nakahara, Y. (1987). "Abuse of Smoking Methamphetamine Mixed with Tobacco: 1. Inhalation Efficiency and Pyrolysis Products of Methamphetamine," Journal of Forensic Science 32(5):1271-1280.

*Vapotronics, Inc.* (1998) located at http://www.vapotronics,com.au/banner.htm., 11 pages, (visited on Jun. 5, 2000).

Wood, R.W. et al. (1996). "Methylecgonidine Coats the Crack Particle." Pharmacology Biochemistry & Behavior. 53(1):57-66.

Wood, R.W. et al. (1996). "Generation of Stable Test Atmospheres of Cocaine Base and Its Pyrolyzate, Methylecgonidine, and Demonstration of Their Biological Activity." Pharmacology Biochemistry & Behavior. 55(2):237-248.

* cited by examiner

RESPIRATORY DRUG CONDENSATION AEROSOLS AND METHODS OF MAKING AND USING THEM

CROSS REFERENCE TO RELATED APPLICATIONS

This application is a continuation of U.S. patent application Ser. No. 10/719,899, filed Nov. 20, 2003, entitled "Respiratory Drug Condensation Aerosols and Methods of Making and Using Them," which claims priority to U.S. Provisional Application Ser. No. 60/429,364 entitled, "Delivery of Asthma Drugs through an Inhalation Route," which was filed on Nov. 26, 2002 each of which is hereby incorporated by reference in its entirety. Any disclaimer that may have occurred during the prosecution of the above-referenced applications is hereby expressly rescinded, and reconsideration of all relevant art is respectfully requested.

BACKGROUND

Asthma is a chronic lung disease affecting millions of people. It is thought to involve three major factors: swelling of the airways, constriction of the muscles around the airways and inflammation. Symptoms of asthma differ widely among sufferers. While some people experience tightness of the chest, wheezing, and difficulty breathing only intermittently, (e.g., with exercise), others experience these symptoms daily.

The precise cause of asthma is not known, but genetic predisposition appears to be an important factor. The most typical triggers of asthma attacks are cold air, exercise, infection, common viruses, irritants, and allergens (e.g., pollen, pet dander, etc.). When the airways come in contact with one of these triggers, the tissue inside the bronchi and bronchioles becomes inflammed and the muscles on the outside of the airways constrict, causing them to narrow. Mucus enters the airways, causing them to swell, and narrow further. Sometimes avoiding the trigger is all that is necessary to prevent an asthma attack. However, avoiding asthma triggers in all instances is seldom possible, so asthma typically requires medical treatment.

There are two primary types of medicines used to treat asthma: the "relievers" and the "controllers" (sometimes also referred to as the "preventers"). Reliever medicines are typically bronchodilators. They are used to provide immediate relief of asthma symptoms (e.g., wheezing, coughing, tightness in the chest, shortness of breath, etc.). Bronchodilators function by dilating, or opening up, the bronchi (i.e., the larger airways delivering air inside the lungs). Most commonly prescribed are the $\beta_2$-adrenoceptor agonists, also referred to as the β-adrenergics (e.g., epinephrine, isoproterenol, albuterol, salmeterol, salbutamol, terbutaline, isoprenaline, isoetharine, metaproterenol, etc.) and the xanthines (e.g., caffeine, theophylline, etc.).

Controllers or preventers, on the other hand, are typically anti-inflammatory medicines. They are medicines taken on a regular basis, even when the asthmatic is not suffering from any symptoms. The goal of these medicines is to prevent asthma symptoms from developing. Controllers function by decreasing the inflammation (e.g., fluid and cellular debris) inside the airways. They are divided into several classes of medications, the most common of which are the corticosteriods. Mediator-release inhibitors and leukotriene modifier agents are also anti-inflammatories used to control asthma. These medicines may also be useful in treating certain respiratory diseases or ailments.

Beyond asthma, other common and/or important respiratory diseases include chronic obstructive pulmonary disease, pulmonary fibrosis (most notably idiopathic pulmonary fibrosis), pulmonary hypertension, and cystic fibrosis. Many of these diseases, especially chronic obstructive pulmonary disease, may be improved by the medications described above for use in asthma.

Chronic obstructive pulmonary disease (COPD) is a common and serious disease strongly associated with cigarette smoking and characterized by chronic productive cough or abnormal permanent enlargement of the alveolar (deep lung) airspaces, accompanied by difficulty moving air in and out of the lungs. This difficulty moving air results shortness of breath on exertion and expiratory wheezes or decreased breath sounds on chest examination. The disease is generally progressive, with severe blood oxygen deficiency and carbon dioxide overload occurring in the late stages. Despite the serious and progressive nature of the underlying pathology of COPD, the disease also frequently involves an airway hyperreactivity (asthma-like) component that may be reversible, resulting in the total obstruction to airflow being partially reversible. COPD is thus sometimes hard to differentiate from unremitting asthma, and the asthma treatments described above are among of the most important treatments for COPD.

Pulmonary fibrosis generally involves chronic inflammation of the alveolar walls with progressive fibrosis. Clinical manifestations include shortness of breath on exertion, nonproductive cough, crackles on chest examination, and, at later stages, digital clubbing and cyanosis. Pulmonary hypertension is an obliterative disease of medium and small pulmonary arteries resulting in heart failure. The key clinical manifestation is progressive exertional shortness of breath. Both of the above diseases have very poor prognosis, frequently resulting in death within 2 to 7 years of diagnosis. Nevertheless, certain respiratory agents, such as anti-endothelin drugs and prostacyclin drugs, provide some survival and/or quality of life benefits.

Cystic fibrosis is an inherited disease of secretory glands, affecting multiple body organs, with a strong respiratory component. It is the most common life-shortening genetic disease in the U.S., and is caused by a genetic defect in a particular chloride-transporting protein, the cystic fibrosis transmembrane regulator. Its respiratory symptoms generally include those of chronic pulmonary obstruction. Beyond the treatments described above, which may be effective in treating the obstructive pulmonary symptoms of cystic fibrosis, other treatments may also be useful, in particular ion channel or pump inhibitors, enhancers, or modulators.

While agents for the treatment of respiratory disease may be delivered by many routes, including systemic routes, many agents effective for the treatment of respiratory disease, e.g., relievers and controllers, are delivered in aerosol form via inhalers. Currently, there are three basic types of inhalers available: nebulizers (jet and ultrasonic), metered dose inhalers, ("MDIs," including MDIs with spacers), and dry powder inhalers ("DPIs"). These inhalers are used for both aerosol generation and aerosol delivery of asthma drugs.

Nebulizers aerosolize liquids and produce a mist of drug-containing water particles for inhalation. There are two basic types of nebulizers, the jet nebulizer, and the ultrasonic nebulizer. Jet nebulizers are more common than ultrasonic nebulizers, because they are less expensive. Typically, with a jet nebulizer, compressed gas flows from an inlet tube over the top of a tube whose end is immersed in a drug solution. The venturi effect creates a pressure drop, which sucks up the liquid and causes it to enter the air stream where it is rapidly dispersed into droplets. The stream of air and water droplets is directed against a baffle, which breaks the droplets into small particles. The small particles are then carried out of the nebulizer suspended in air, and the remaining droplets reenter the solution. With ultrasonic nebulizers, particles are produced by mechanical vibration of a plate or mesh using a piezoelectric crystal.

With MDIs, a measured (i.e., metered) dose of medicine is dispensed into the user's mouth using a small amount of pressurized gas (i.e., a propellant). Sometimes a spacer is placed between the drug reservoir and the user's mouth in order to control the amount of aerosol that is inhaled. The aerosol of a MDI is created when a valve is opened (usually by pressing down on a propellant canister), allowing liquid propellant to spray out by cavitation. The drug is usually contained in small particles suspended in the liquid propellant, but in some formulations the drug is dissolved in the propellant. In either case, the propellant evaporates rapidly as the aerosol leaves the device, resulting in small drug particles that are inhaled. Prior to the mid 1990s, MDIs used various chlorofluorocarbons ("CFCs") as their propellant, but with the elimination of CFCs in industry due to ozone depletion concerns, the propellants in new MDIs typically use hydrofluoroalkanes ("HFAs").

Unlike the aerosols discussed above, the aerosols produced by DPIs are in the form of a powder. Typically the asthma drugs of DPIs are manufactured in powder form as small powder particles of a few micrometers in diameter. The asthma drug is then typically mixed with larger sugar particles, for example, lactose monohydrate, (e.g., typically 50-100 micrometers in diameter). The asthma drug particles attach to the excipient lactose particles. The increased aerodynamic forces on the lactose/drug agglomerates are thought to improve entrainment of the small drug particles upon inhalation. Upon inhalation, the powder is broken into its constituent particles with the aid of turbulence and, in some instances, mechanical devices such as screens or spinning surfaces. Dry powder formulations, while offering advantages over the cumbersome liquid nebulizer formulations, and the propellant-driven formulations, are prone to aggregation and low flowability phenomena which considerably diminish the efficiency of the dry powder-based inhalation therapies.

Despite the variety of inhalation devices available, these devices are suboptimal in numerous respects. For example, MDIs need to be shaken prior to use. Many users fail to shake the MDIs and therefore receive inconsistent amounts of medication. Other times, the MDI ejects the drug with such a great exit velocity or in such a large particle size that the drug collides with the back of the throat and does not reach the lung in substantial quantity. For nebulizers, undesirably large particle size is also a common problem, as is slow aerosolization of the drug. Because of slow aerosol generation, nebulizer treatments often require a patient to inhale on the nebulizer for minutes to hours to receive a therapeutic amount of medication, disrupting the patient's other life activities or providing unacceptably slow relief of an acute asthma attack. Another problem with liquid inhalers such as nebulizers is that delivery of liquids other than neutral pH saline to the lungs may irritate the lungs, whereas saline may provide a vehicle that carries bacteria or other pathogens into the lungs. Also, many important drugs are not soluble in neutral pH saline. For dry powder inhalers, undesirably large particle size is again a problem. The problem is particularly severe for patients who cannot inhale with much vigor, because vigorous inhalation is generally required to disperse the powder. Because respiratory patients in need of inhaled medications frequently have impaired abilities to inhale, the above problem of strong inhalation being required to disperse dry powders is particularly clinically significant. Another problem with dry powders is that they contain additives such as lactose, generally in quantities exceeding the quantity of drug in the inhaler. Such additives may irritate or otherwise damage the lung, while providing no therapeutic benefits.

Accordingly, it would be desirable to provide improved respiratory drug aerosols and improved inhalation devices for administering such aerosols.

SUMMARY

Described herein are respiratory drug condensation aerosols and methods of making and using them. Kits for delivering a condensation aerosol are also described. The respiratory drug aerosols described herein typically comprise respiratory drug condensation aerosol particles. In some variations the particles comprise a respiratory drug selected from the group consisting of β-adrenergics, methylxanthines, anticholinergics, corticosteroids, mediator-release inhibitors, anti-leukotriene drugs, asthma inhibitors, asthma antagonists, anti-endothelin drugs, prostacyclin drugs, ion channel or pump inhibitors, enhancers, or modulators and pharmaceutically acceptable analogs, derivatives, and mixtures thereof. In other variations, the respiratory drug is selected from the group consisting of albuterol, epinephrine, metaproterenol, terbutaline, pseudoephedrine hydrochloride, bambuterol, bitolterol, carbuterol, clenbuterol, clorprenalin, dioxethedrine, eprozinol, etefedrine, ethylnorepinephrine, fenoterol, fenspiride, hexoprenaline, isoetharine, isoproterenol, mabuterol, methoxyphenamine, pirbuterol, procaterol, protokylol, rimiterol, salmeterol, soterenol, tretoquinol, tulobuterol, caffeine, theophylline, aminophylline, acefylline, bamifylline, doxofylline, dyphylline, etamiphyllin, etofylline, proxyphylline, reproterol, theobromine-1-acetic acid, atropine, ipratropium bromide, flutropium bromide, oxitropium bromide, tiotropium bromide, budesonide, beclomethasone, ciclesonide, dexamethasone, flunisolide, fluticasone propionate, triamcinolone acetonide, prednisolone, methylprednisolone, hydrocortisone, cromolyn sodium, nedocromil sodium, montelukast, zafirlukast, pirfenidone, CPX, IBMX, cilomilast, roflumilast, pumafentrine, domitroban, israpafant, ramatroban, seratrodast, tiaramide, zileuton, ambrisentan, bosentan, enrasentan, sitaxsentan, tezosentan, iloprost, treprostinil, and pharmaceutically acceptable analogs, derivatives, and mixtures thereof.

In some variations, the aerosol comprises at least 50% by weight of a respiratory drug. In other variations the aerosol comprises at least 75% or 95% by weight of the respiratory drug. Similarly, in some variations, the aerosol is substantially free of thermal degradation products, and in some variations, the respiratory drug condensation aerosol has a MMAD in the range of 2-4 μm. In some variations, the respiratory drug condensation aerosol has a MMAD in the range of 10 nm-100 nm. In some variations, the aerosol comprises two or more therapeutically active respiratory drugs. In some variations, the aerosol comprises both a β-adrenergic drug and a corticosteroid.

The kit for delivering a respiratory drug condensation aerosol typically comprises a composition comprising a respiratory drug, and a device for forming a respiratory drug aerosol. The device for forming a respiratory drug aerosol typically comprises an element configured to heat the composition to form a vapor, an element allowing the vapor to condense to form a condensation aerosol, and an element permitting a user to inhale the condensation aerosol. The composition may further comprise a pharmaceutically acceptable excipient, and the device may further comprise features such as breath-actuation or lockout elements.

Methods of treating respiratory ailments using the aerosols described herein are also provided. In general, the method comprises the step of administering a therapeutically effective amount of a respiratory drug condensation aerosol to a person with a respiratory ailment. In some variations, the method for treating a respiratory ailment comprises the step of administering a therapeutically effective amount of a respiratory drug aerosol to a person with the respiratory ailment, wherein the respiratory drug aerosol comprises a respiratory drug and has a MMAD in the range of about 2-4 μm. The respiratory drug condensation aerosol may be administered in a single inhalation, or may be administered in more than one inhalation. In some variations, the respiratory drug condensation aerosol has a purity greater than 90%. In some variations, the respiratory drug condensation aerosol comprises two or more therapeutically active respiratory drugs. In some variations, the drug condensation aerosol comprising two or more respiratory drugs has a purity of greater than 90%. In some variations, the purity of each of the respiratory drugs present in the aerosol is greater than 90%.

Methods of forming a respiratory drug condensation aerosol are also described. The methods of forming a respiratory drug condensation aerosol typically comprise the steps of providing a respiratory drug composition in a unit dose form, vaporizing the respiratory drug composition, and condensing the respiratory drug composition. The step of vaporizing the respiratory drug composition typically comprises the step of heating the composition to form a vapor.

The composition typically comprises one or more respiratory drug selected from the group consisting of β-adrenergics, methylxanthines, anticholinergics, corticosteroids, mediator-release inhibitors, anti-leukotriene drugs, asthma inhibitors, asthma antagonists, anti-endothelin drugs, prostacyclin drugs, ion channel or pump inhibitors, enhancers, or modulators and pharmaceutically acceptable analogs, derivatives, and mixtures thereof. In other variations, the asthma drug is selected from the group consisting of albuterol, epinephrine, metaproterenol, terbutaline, pseudoephedrine hydrochloride, bambuterol, bitolterol, carbuterol, clenbuterol, clorprenalin, dioxethedrine, eprozinol, etefedrine, ethylnorepinephrine, fenoterol, fenspiride, hexoprenaline, isoetharine, isoproterenol, mabuterol, methoxyphenamine, pirbuterol, procaterol, protokylol, rimiterol, salmeterol, soterenol, tretoquinol, tulobuterol, caffeine, theophylline, aminophylline, acefylline, bamifylline, doxofylline, dyphylline, etamiphyllin, etofylline, proxyphylline, reproterol, theobromine-1-acetic acid, atropine, ipratropium bromide, flutropium bromide, oxitropium bromide, tiotropium bromide, budesonide, beclomethasone, ciclesonide, dexamethasone, flunisolide, fluticasone propionate, triamcinolone acetonide, prednisolone, methylprednisolone, hydrocortisone, cromolyn sodium, nedocromil sodium, montelukast, zafirlukast, pirfenidone, CPX, IBMX, cilomilast, roflumilast, pumafentrine, domitroban, israpafant, ramatroban, seratrodast, tiaramide, zileuton, ambrisentan, bosentan, enrasentan, sitaxsentan, tezosentan, iloprost, treprostinil, and pharmaceutically acceptable analogs, derivatives, and mixtures thereof.

DETAILED DESCRIPTION

Definitions

Figure 1:
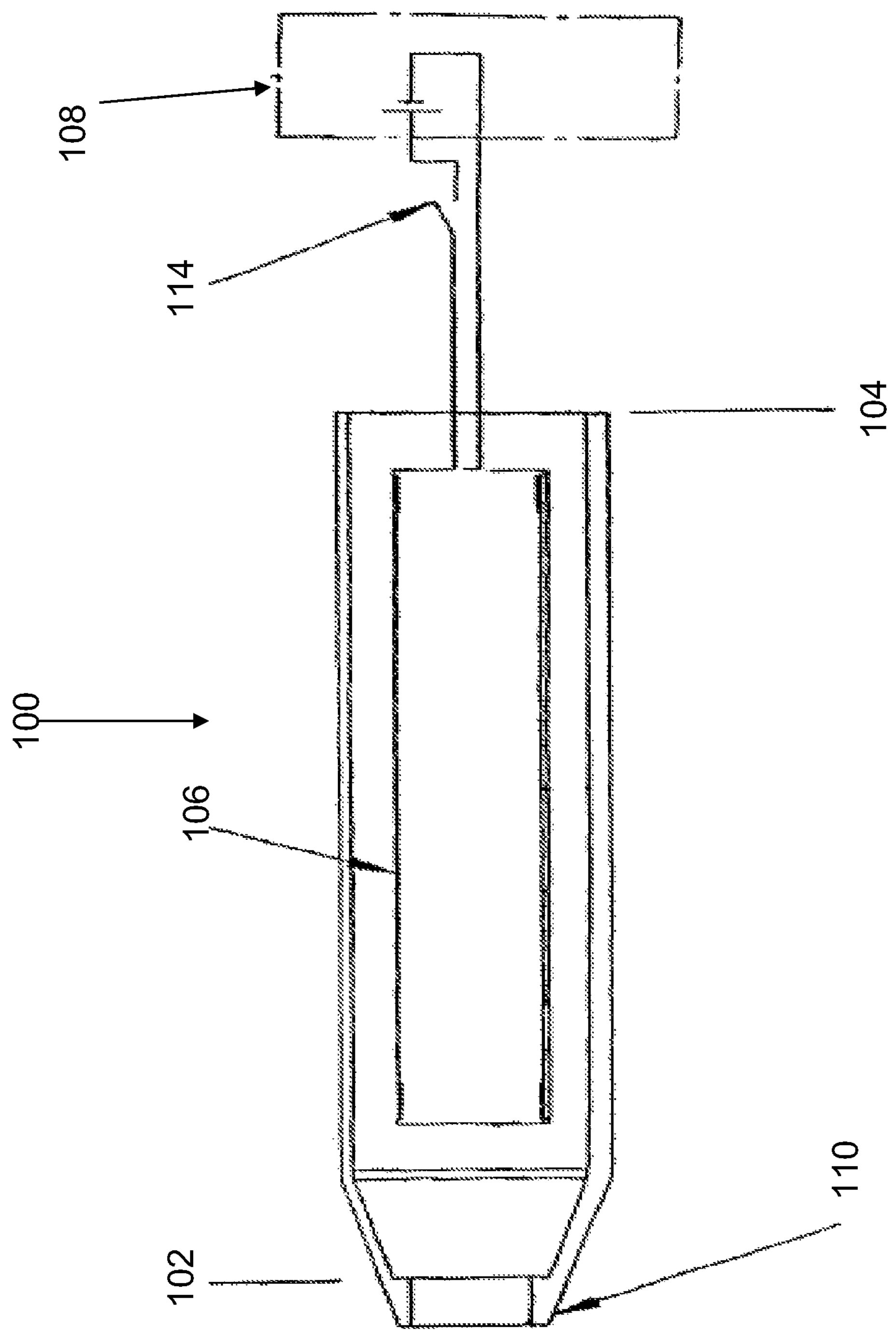
FIG. 1 is an illustration of an exemplary device that may be used to form and administer the aerosols described herein.

As defined herein, the following terms shall have the following meanings when reference is made to them throughout the specification.

"Condensation aerosol" refers to an aerosol that has been formed by the vaporization and subsequent cooling of the vapor, such that the vapor condenses to form particles.

"Controllers" or "preventers" are used herein interchangably and refer to drugs that are anti-inflammatory medicines.

"Heat stable drug" refers to a drug that has a TSR$\geqq$9 when vaporized from a film of some thickness between 0.05 μm and 20 μm.

"Mass median aerodynamic diameter" or "MMAD" of an aerosol refers to the aerodynamic diameter for which half the particulate mass of the aerosol is contributed by particles with an aerodynamic diameter larger than the MMAD and half by particles with an aerodynamic diameter smaller than the MMAD.

"Purity" as used herein, with respect to the aerosol purity, means (the fraction of drug in the aerosol/the fraction of drug in the aerosol plus drug degradation products in the aerosol). In the case where an aerosol contains more than one drug, purity may be reported as [the fraction of drug composition (summed for all of the drugs in the aerosol)/the fraction of the drug composition in the aerosol plus drug degradation products in the aerosol (summed for all of the drugs in the aerosol)]. Alternatively, if it is known which parent drug gives rise to each of the drug degradation products present in the aerosol in significant amounts, the purity may be reported for each drug in the aerosol as (the fraction of the specific drug in the aerosol/the fraction of that drug plus that drug's degradation products) in the aerosol.

"Reliever" refers to a drug that is a bronchodilator.

"Substantially free of thermal degradation products" means that the aerosol is at least 50% free of thermal degradation products.

"Therapeutically effective amount" means the amount required to achieve a therapeutic effect. The therapeutic effect could be any therapeutic effect ranging from prevention, symptom amelioration, symptom treatment, to disease termination or cure.

"Thermal degradation product" means any byproduct, which results from heating the respiratory drug composition and is not responsible for producing a therapeutic effect.

"Thermal stability ratio" or "TSR" means the % purity/(100%-% purity) if the % purity is <99.9%, and 1000 if the % purity is $\geqq$99.9%. For example, a respiratory drug vaporizing at 90% purity would have a TSR of 9. An example of how to determine whether a respiratory drug is heat stable is provided below.

"Vapor" refers to a gas, and "vapor phase" refers to a gas phase. The term "thermal vapor" refers to a vapor phase, aerosol, or mixture of aerosol-vapor phases, formed preferably by heating.

Respiratory Drug Compositions

The respiratory drug compositions described herein typically comprise at least one asthma drug, chronic obstructive pulmonary disease drug, pulmonary hypertension drug, pulmonary fibrosis drug, and/or cystic fibrosis drug. It should be understood that when reference is made herein to a "respiratory drug" it is intended that this phrase includes those drugs described herein, which may also be useful in treating asthma, as well as certain respiratory ailments or diseases (e.g., chronic obstructive pulmonary disease, pulmonary hypertension, pulmonary fibrosis, cystic fibrosis, and the like). The respiratory drug compositions may comprise other compounds as well. For example, the respiratory drug composition may comprise a mixture of respiratory drugs, a mixture of a respiratory drug and a pharmaceutically acceptable excipient, or a mixture of a respiratory drug with other compounds having useful or desirable properties. The respiratory drug composition may comprise a pure respiratory drug as well.

Any suitable respiratory drug may be used. In general, we have found that suitable respiratory drugs have properties that make them acceptable candidates for use with the devices and methods herein described. For example, the respiratory drug is typically one that is, or can be made to be, vaporizable.

Classes of bronchodilator drugs suitable for use with the described methods and devices include the β-adrenergics, the methylxanthines, and the anticholinergics. Classes of anti-inflammatory drugs suitable for use with the described methods and devices include the corticosteroids, the mediator-release inhibitors, the anti-leukotriene drugs, as well as other inhibitors or antagonists. Other classes of respiratory drugs suitable for use with the described methods and devices include anti-endothelin drugs and prostacyclin drugs, which are particularly useful in the treatment of pulmonary fibrosis or hypertension, and ion channel or pump inhibitors, enhancers, and modulators, which are particularly useful in the treatment of cystic fibrosis. Exemplary β-adrenergics include, without limitation, albuterol, epinephrine, metaproterenol, terbutaline, pseudoephedrine hydrochloride, bambuterol, bitolterol, carbuterol, clenbuterol, clorprenalin, dioxethedrine, eprozinol, etefedrine, ethylnorepinephrine, fenoterol, fenspiride, hexoprenaline, isoetharine, isoproterenol, mabuterol, methoxyphenamine, pirbuterol, procaterol, protokylol, rimiterol, salmeterol, soterenol, tretoquinol, tulobuterol, and pharmaceutically acceptable analogs, derivatives, and mixtures thereof. Exemplary methylxanthines include, without limitation, caffeine, theophylline, aminophylline, acefylline, bamifylline, doxofylline, dyphylline, etamiphyllin, etofylline, proxyphylline, reproterol, theobromine-1-acetic acid, and pharmaceutically acceptable analogs, derivatives, and mixtures thereof. Exemplary anticholinergics include, without limitation, atropine, ipratropium bromide, flutropium bromide, oxitropium bromide, tiotropium bromide, and pharmaceutically acceptable analogs, derivatives, and mixtures thereof.

Similarly, exemplary corticosteroids include, without limitation, budesonide, beclomethasone, ciclesonide, dexamethasone, flunisolide, fluticasone propionate, triamcinolone acetonide, prednisolone, methylprednisolone, hydrocortisone, and pharmaceutically acceptable analogs, derivatives, and mixtures thereof. Exemplary mediator-release inhibitors include, without limitation, cromolyn sodium, nedocromil sodium, and pharmaceutically acceptable analogs, derivatives, and mixtures thereof. Exemplary anti-leukotrienes include, without limitation, montelukast, zafirlukast, and pharmaceutically acceptable analogs, derivatives, and mixtures thereof. Other suitable respiratory drugs include, without limitation, pirfenidone, CPX, IBMX, cilomilast, roflumilast, pumafentrine, domitroban, israpafant, ramatroban, seratrodast, tiaramide, zileuton, ambrisentan, bosentan, enrasentan, sitaxsentan, tezosentan, iloprost, treprostinil, and pharmaceutically acceptable analogs, derivatives, and mixtures thereof.

Tables providing chemical structures and some physical properties for a few of these illustrative compounds are provided below.

TABLE 1

| SUITABLE β-ADRENERGIC DRUGS |
|---|
| Albuterol |
| 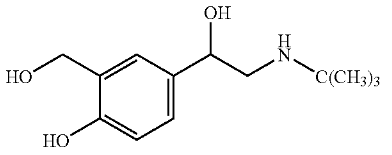 |
| MW: 239<br>MP: 158° C. |
| Epinephrine |
| 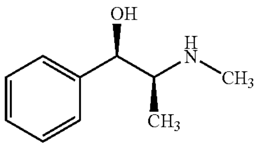 |
| MW: 165<br>MP: 40° C. |
| Metaproterenol |
| 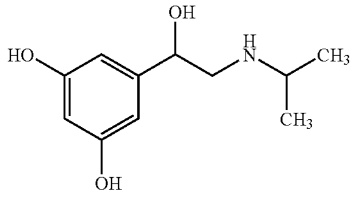 |
| MW: 211<br>MP: 100° C. |
| Terbutaline |
| 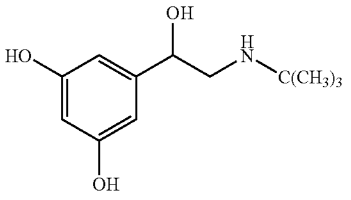 |
| MW: 225<br>MP: 122° C. |

TABLE 1-continued
| SUITABLE β-ADRENERGIC DRUGS |
|---|
Pseudoephedrine Hydrochloride
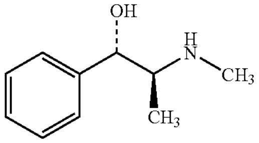
MW: 202
MP: 184° C.
Bambuterol
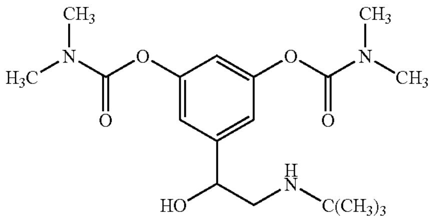
MW: 367
Bitolterol
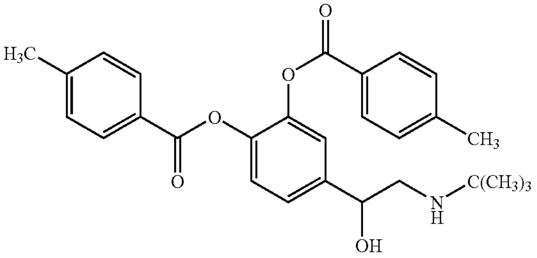
MW: 462
Carbuterol
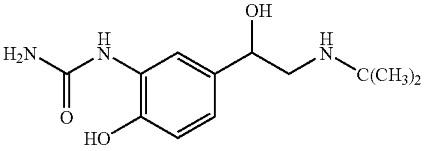
MW: 267
MP: 174
Clenbuterol
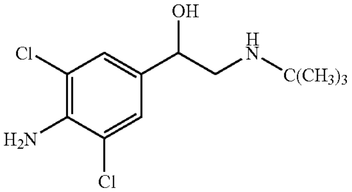
MW: 277
TABLE 1-continued
| SUITABLE β-ADRENERGIC DRUGS |
|---|
Clorprenalin
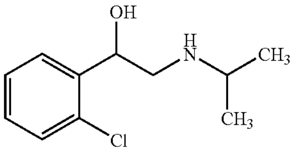
MW: 214
Dioxethedrine
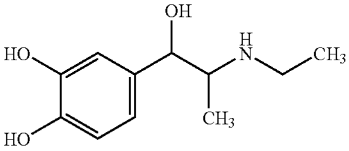
MW: 211
Eprozinol
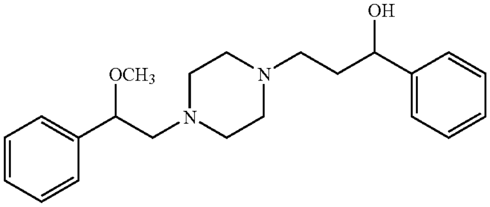
MW: 354
Etefedrine
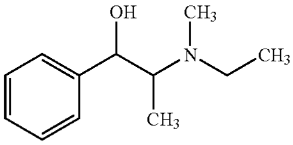
MW: 193
Ethylnorepinephrine
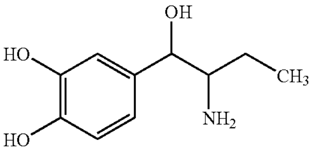
MW: 197

TABLE 1-continued
SUITABLE β-ADRENERGIC DRUGS
Fenoterol
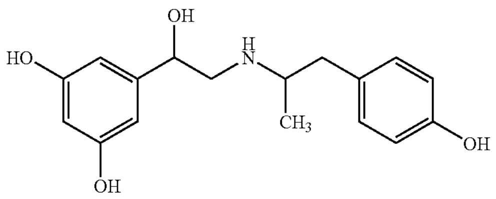
MW: 303
Fenspiride
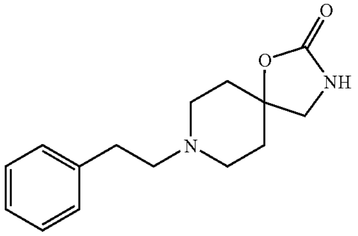
MW: 260
Hexoprenaline
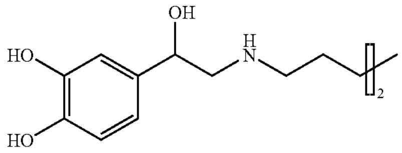
MW: 421
MP: 162° C.
Isoetharine
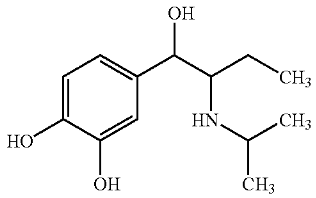
MW: 239
Isoproterenol
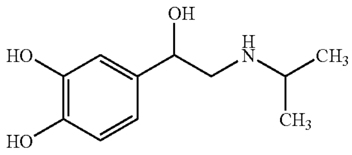
MW: 211
MP: 155° C.
TABLE 1-continued
SUITABLE β-ADRENERGIC DRUGS
Mabuterol
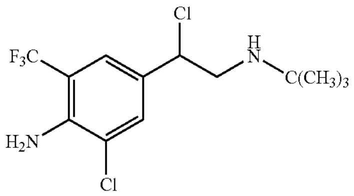
MW: 311
Methoxyphenamide
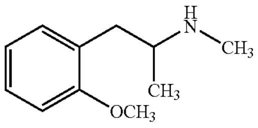
MW: 179
Pirbuterol
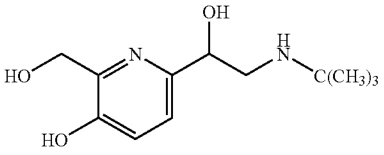
MW: 240
Procaterol
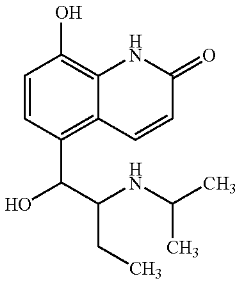
MW: 290
Protokylol
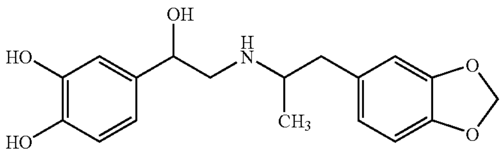
MW: 331

TABLE 1-continued
SUITABLE β-ADRENERGIC DRUGS
Rimiterol
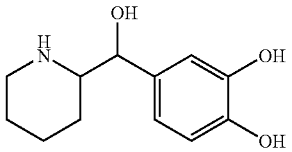
MW: 223
MP: 203° C.
Salmeterol
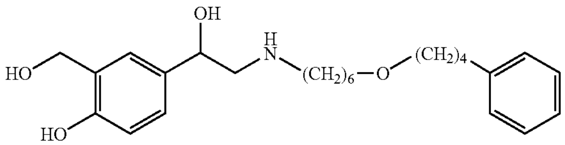
MW: 416
MP: 76
Soterenol
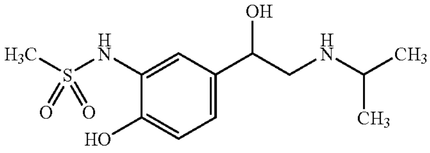
MW: 288
Tretoquinol
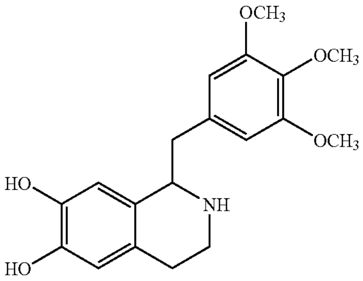
MW: 345
Tulobuterol
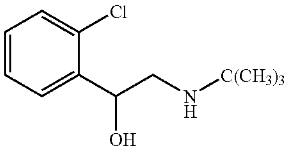
MW: 228
MP: 89° C.
TABLE 2
SUITABLE METHYL XANTHINE DRUGS
Theophylline
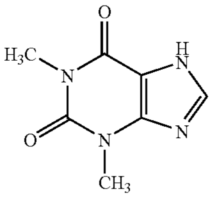
MW: 180
MP: 274° C.
Acefylline
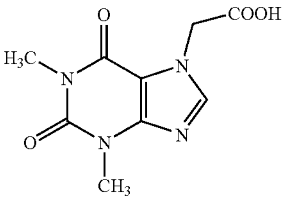
MW: 238
MP: 271° C.
Bamifylline
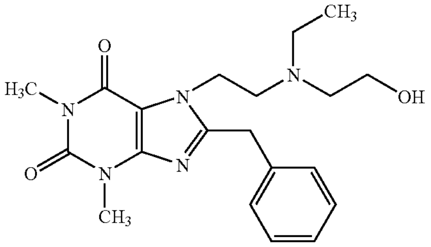
MW: 385
MP: 80° C.
Doxofylline
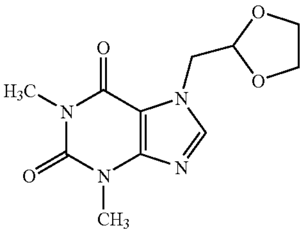
MW: 266
MP: 144° C.

TABLE 2-continued
| SUITABLE METHYL XANTHINE DRUGS |
|---|
| Dyphylline |
| 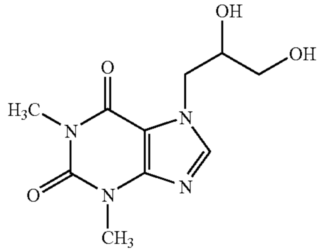 |
| MW: 254<br>MP: 158° C. |
| Etamiphyllin |
| 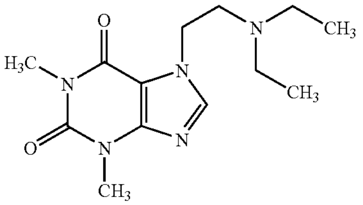 |
| MW: 279<br>MP: 75° C. |
| Etofylline |
| 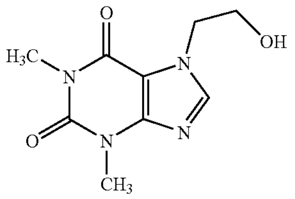 |
| MW: 222<br>MP: 158° C. |
| Proxyphylline |
| 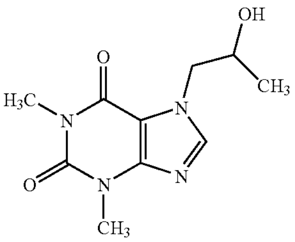 |
| MW: 238<br>MP: 135° C. |
TABLE 2-continued
| SUITABLE METHYL XANTHINE DRUGS |
|---|
| Reproterol |
| 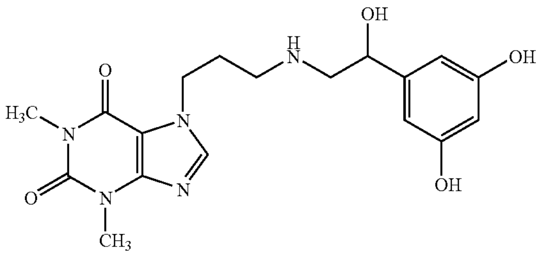 |
| MW: 389 |
| Theobromine-1-acetic acid |
| 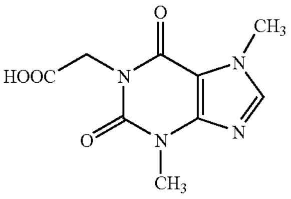 |
| MW: 238<br>MP: 260° C. |
TABLE 3
| SUITABLE ANTICHOLINERGIC DRUGS |
|---|
| Ipratropium Bromide |
| 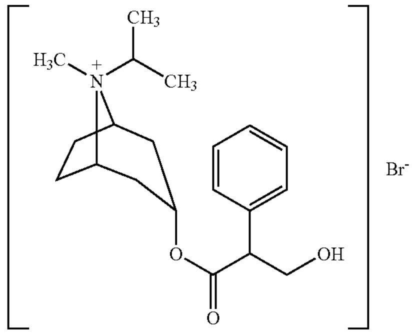 |
| MW: 412<br>MP: 232° C. |

TABLE 3-continued
| SUITABLE ANTICHOLINERGIC DRUGS |
|---|
Flutropium Bromide
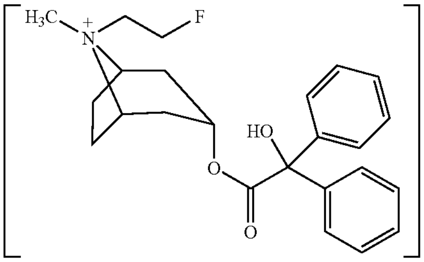
MP: 192° C.
Oxitropium Bromide
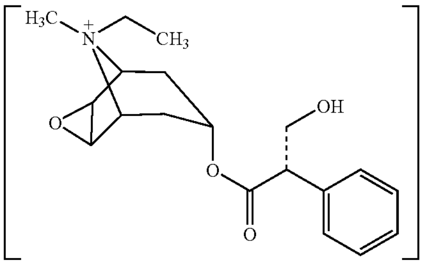
MW: 412
MP: 203° C.
Tiotropium Bromide
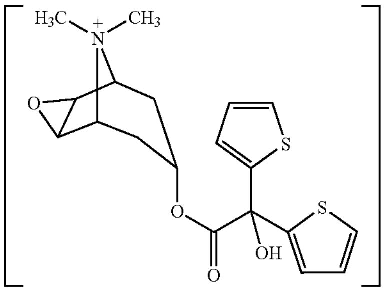
MW: 472
MP: 218° C.
TABLE 4
| SUITABLE CORTICOSTEROID DRUGS |
|---|
Budesonide
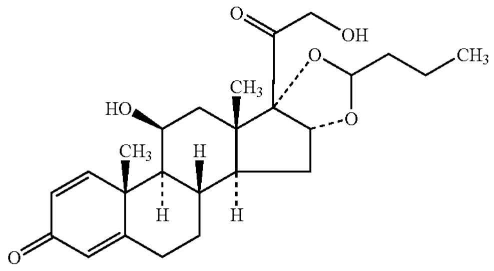
MW: 431
MP: 232° C.
Ciclesonide
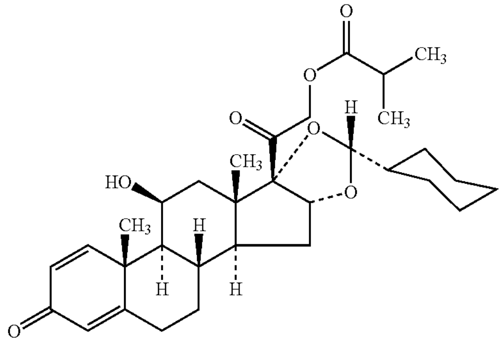
MW: 541
Dexamethasone
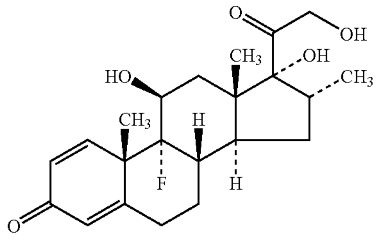
MW: 392
MP: 271° C.
Flunisolide
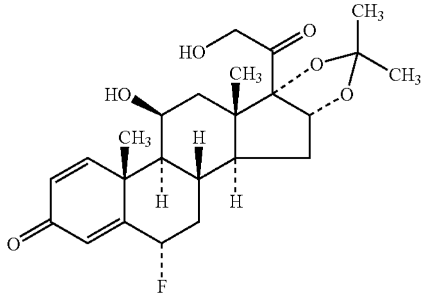
MW: 431

TABLE 4-continued
| SUITABLE CORTICOSTEROID DRUGS |
|---|
| Fluticasone Propionate |
| 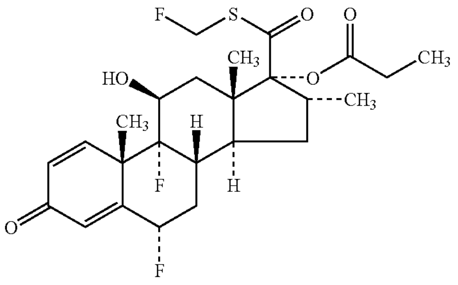 |
| MW: 501<br>MP: 272° C. |
| Triamcinolone Acetonide |
| 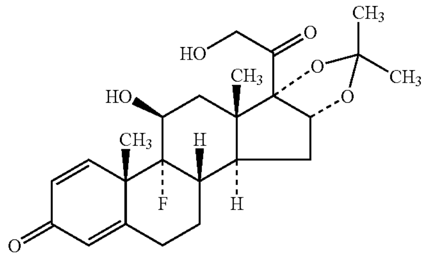 |
| MW: 434<br>MP: 294° C. |
TABLE 5
| SUITABLE INHIBITOR OR ANTAGONIST DRUGS |
|---|
| Pirfenidone |
| 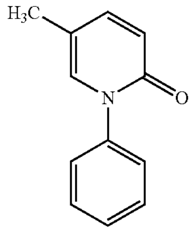 |
| MW: 185<br>MP: 102° C. |
| CPX |
| 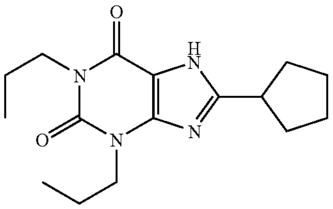 |
| MW: 304<br>MP: 191° C. |
TABLE 5-continued
| SUITABLE INHIBITOR OR ANTAGONIST DRUGS |
|---|
| IBMX |
| 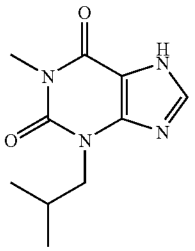 |
| MW: 222 |
| Cilomilast |
| 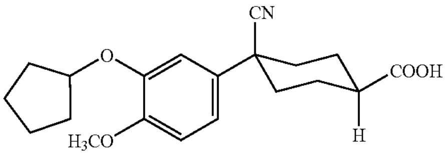 |
| MW: 343<br>MP: 157° C. |
| Roflumilast |
| 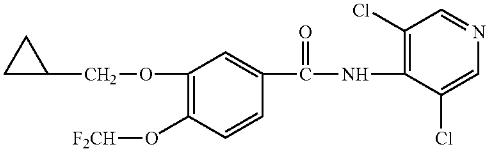 |
| Pumafentrine |
| 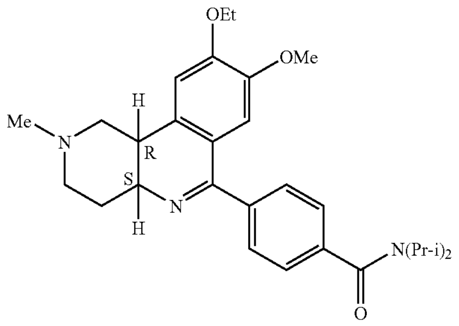 |
| Domitroban |
| 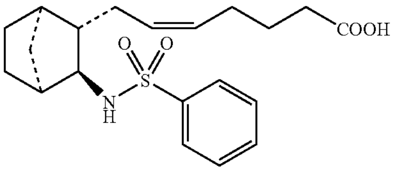 |
| MW: 378<br>MP: 60° C. |

TABLE 5-continued
| SUITABLE INHIBITOR OR ANTAGONIST DRUGS |
|---|
| Israpafant |
| 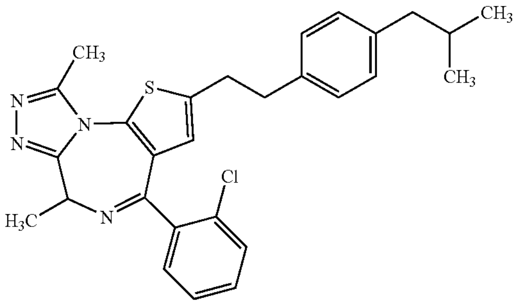 |
| MW: 489<br>MP: 130° C. |
| Ramatroban |
| 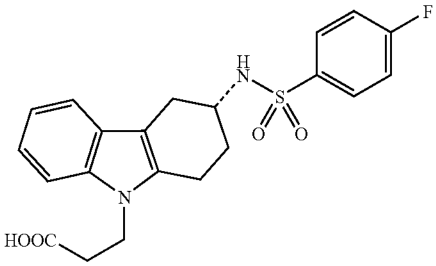 |
| MW: 416<br>MP: 134° C. |
| Seratrodast |
| 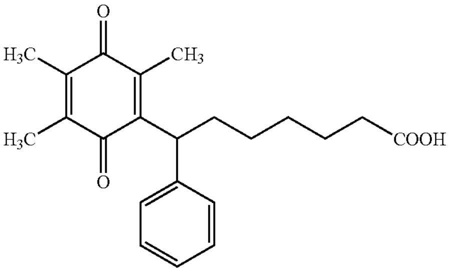 |
| MW: 354<br>MP: 128° C. |
| Tiaramide |
| 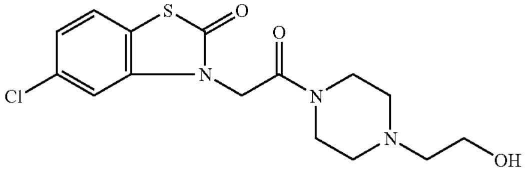 |
| MW: 356 |
TABLE 5-continued
| SUITABLE INHIBITOR OR ANTAGONIST DRUGS |
|---|
| Zileuton |
| 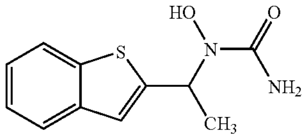 |
| MW: 236<br>MP: 157° C. |
TABLE 6
| SUITABLE ANTI-LEUKOTRIENE DRUGS |
|---|
| Montelukast |
| 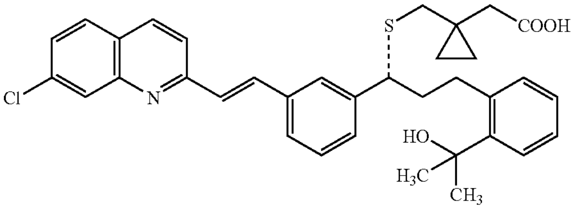 |
| MW: 586 |
| Zafirlukast |
| 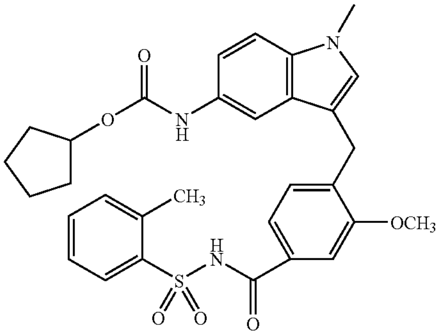 |
| MW: 576<br>MP: 140° C. |
| Pranlukast |
| 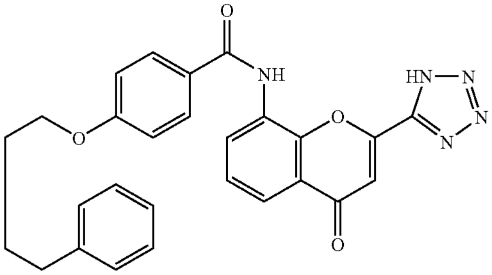 |
| MW: 482<br>MP: 244° C. |

TABLE 7

| SUITABLE ANTI-ENDOTHELIN DRUGS |
| --- |
| Bosentan |
| 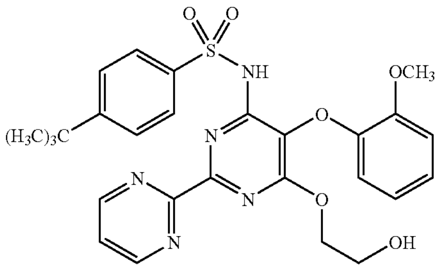 |
| MW: 552 |
| Ambrisentan |
| 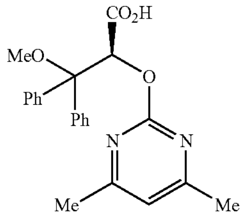 |
| MW: 378 |
| Sitaxsentan |
| 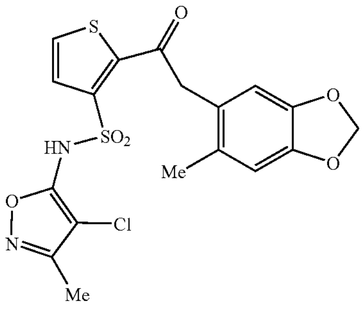 |
| MW: 455 |

TABLE 8

| SUITABLE PROSTACYCLIN DRUGS |
| --- |
| Treprostinil |
| 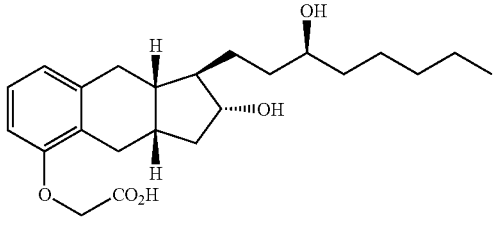 |
| MW: 391 |

TABLE 8-continued

| SUITABLE PROSTACYCLIN DRUGS |
| --- |
| Iloprost |
| 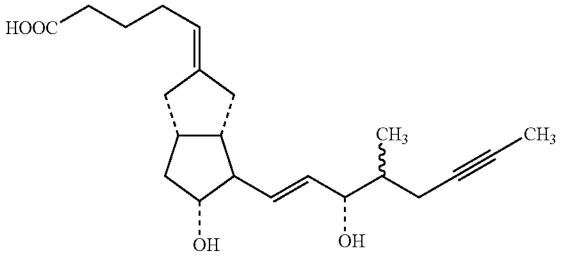 |
| MW: 361 |

Typically, the respiratory drug is in its free base, free acid or ester form. However, it is not without possibility that the respiratory drug can be vaporizable from its salt form as well. Indeed, a variety of pharmaceutically acceptable salts are suitable for aerosolization. Illustrative salts include, without limitation, the following: sodium, potassium, or other alkali metal salts, and ammonium or substituted ammonium salts, hydrochloric acid, hydrobromic acid, acetic acid, maleic acid, formic acid, and fumaric acid salts. Salt forms of respiratory drugs can be obtained from their corresponding free base or free acid forms using well known methods in the art.

Suitable pharmaceutically acceptable excipients may be volatile or nonvolatile. Volatile excipients, when heated, are concurrently volatilized, aerosolized and inhaled with the asthma drug. Classes of such excipients are known in the art and include, without limitation, gaseous, supercritical fluid, liquid and solid solvents. The following is a list of exemplary carriers within these classes: water; terpenes, such as menthol; alcohols, such as ethanol, propylene glycol, glycerol and other similar alcohols; dimethylformamide; dimethylacetamide; wax; supercritical carbon dioxide; dry ice; and mixtures thereof.

Solid Support

Typically, the respiratory drug composition is coated on a solid support and the solid support is heated to vaporize the asthma drug composition. The support may be of any geometry and a variety of different sizes. It is often desirable that the solid support provide a large surface to volume ratio (e.g., greater than 100 per meter) and a large surface to mass ratio (e.g., greater than 1 $cm^2$ per gram).

A solid support of one shape can also be transformed into another shape with different properties. For example, a flat sheet of 0.25 mm thickness has a surface to volume ratio of approximately 8,000 per meter. Rolling the sheet into a hollow cylinder of 1 cm diameter produces a support that retains the high surface to mass ratio of the original sheet but has a lower surface to volume ratio (about 400 per meter).

A number of different materials may be used to construct the solid supports. Classes of such materials include, without limitation, metals, inorganic materials, carbonaceous materials, and polymers. Illustrative materials within these classes are aluminum, silver, iron, gold, stainless steel, copper and tungsten; silica, glass, silicon and alumina; graphite, ceramics; and polytetrafluoroethylene. In one variation, the solid support is stainless steel. Combinations of materials and coated variants of materials may be used as well.

When it is desirable to use aluminum as a solid support, aluminum foil is a suitable material. Examples of alumina and silicon based materials include BCR171 (an alumina of defined surface area greater than 2 $m^2/g$ from Aldrich, St. Louis, Mo.) and a silicon wafer as used in the semiconductor industry. Chromatography resins such as octadecycl silane chemically bonded to porous silica are exemplary coated variants of silica.

Typically it is desirable that the solid support have relatively few, or substantially no, surface irregularities. Although a variety of supports may be used, supports that have an impermeable surface, or an impermeable surface coating, are typically desirable. Illustrative examples of such supports include metal foils, smooth metal surfaces, nonporous ceramics, and the like.

The respiratory drug composition is typically coated on the solid support in the form of a film. The film may be coated on the solid support using any suitable method. The method suitable for coating is often dependent upon the physical properties of the respiratory drug and the desired film thickness. One exemplary method of coating a respiratory drug composition on a solid support is by preparing a solution of respiratory drug (alone or in combination with other desirable compounds) in a suitable solvent, applying the solution to the exterior surface of the solid support, and then removing the solvent (e.g., via evaporation, etc.) thereby leaving a film on the support surface.

Common solvents include methanol, dichloromethane, methyl ethyl ketone, diethyl ether, 3:1 chloroform:methanol mixture, 1:1 dichloromethane: methyl ethyl ketone mixture, dimethylformamide, and deionized water. Sonication may also be used as necessary to dissolve the respiratory drug.

The respiratory drug composition may also be coated on the solid support by dipping the support into a respiratory drug composition solution, or by spraying, brushing or otherwise applying the solution to the support. Alternatively, a melt of the drug can be prepared and applied to the support. For drugs that are liquids at room temperature, thickening agents can be mixed with the drug to permit application of a solid drug film.

Formation of Respiratory Drug Condensation Aerosols

Any suitable method may be used to form the respiratory drug aerosols described herein. One such method involves the heating of a respiratory drug composition to form a vapor, followed by cooling of the vapor so that it forms an aerosol (i.e., a condensation aerosol). Exemplary methods of heating include the passage of current through an electrical resistance element, absorption of electromagnetic radiation (e.g., microwave or laser light) and exothermic chemical reactions (e.g., exothermic salvation, hydration of pyrophoric materials, and oxidation of combustible materials). Heating of the substrate by conductive heating is also suitable. One exemplary heating source is described in U.S. patent application for SELF-CONTAINED HEATING UNIT AND DRUG-SUPPLY UNIT EMPLOYING SAME, U.S. Ser. No. 60/472,697 filed May 21, 2003. The description of the exemplary heating source disclosed therein, is hereby incorporated by reference.

Heat sources or devices that contain a chemically reactive material are also suitable. Typically the chemically reactive material undergoes an exothermic reaction upon actuation, e.g., by a spark or other heat element, such as a flashbulb type heater, or other heaters such as described in U.S. patent application for SELF-CONTAINED HEATING UNIT AND DRUG-SUPPLY UNIT EMPLOYING SAME. In particular, heat sources that generate heat by exothermic reaction, where the chemical "load" of the source is consumed in a period of between 50-500 msec or less are generally suitable, assuming good thermal coupling between the heat source and substrate.

In one method, the heating of the respiratory drug composition involves heating a thin film of the composition having a thickness between about 0.05 μm-20 μm to form a vapor. In yet other variations, the composition has a film thickness between about 0.5 μm-10 μm. Most typically, the film thickness vaporized is between 0.5 μm-5 μm.

In some variations, the respiratory drug condensation aerosol comprises at least 5% by weight of asthma drug condensation aerosol particles. In other variations, the aerosol comprises at least 10%, 20%, 30%, 40%, 50%, 60%, or 75% by weight of asthma drug condensation aerosol particles. In still other variations, the aerosol comprises at least 95%, 99%, or 99.5% by weight of respiratory drug condensation aerosol particles.

In some variations, the respiratory drug condensation aerosol particles comprise less than 10% by weight of a thermal degradation product. In other variations, the respiratory drug condensation aerosol particles comprise less than 5%, 1%, 0.5%, 0.1%, or 0.03% by weight of a thermal degradation product.

In some variations, the respiratory drug condensation aerosol has a MMAD of less than 5 microns, or less than 3 microns. In other variations the respiratory drug condensation aerosol has a MMAD in the range of about 1-5 μm, 1.5-4.5 μm, 1.5-4 μm, 1.8-4 μm, 1-3 μm, or 2-3 μm. In other variations the respiratory drug condensation aerosol has a MMAD in the range of about 10-100 nm, 10-200 nm or of about 10-300 nm. In some variations the geometric standard deviation around the MMAD of the respiratory drug condensation aerosol particles is less than 3.0. In other variations, the geometric standard deviation around the MMAD of the respiratory drug condensation aerosol particles is less than 2.5, or less than 2.0.

The aerosol particles for administration can typically be formed using any of the described methods at a rate of greater than $10^8$ inhalable particles per second. In some variations, the aerosol particles for administration are formed at a rate of greater than $10^9$ or $10^{10}$ inhalable particles per second. With respect to the rate of aerosol formation (i.e., the mass of aerosolized particulate matter produced by a delivery device per unit time) the aerosol may be formed at a rate greater than 0.25 mg/second, greater than 0.5 mg/second, or greater than 1 or 2 mg/second. Similarly, with respect to the rate of drug aerosol formation (i.e., the mass of aerosolized drug produced by a delivery device per unit time) the drug aerosol may be formed at a rate in the range of from about 0.03 mg/second to about 2 mg/second. Alternatively or in addition, the rate of drug aerosol formation may be greater than 0.01 mg/s, 0.03 mg/s, 0.05 mg/s, 0.09 mg/s, 0.15 mg/s, 0.25 mg/s, 0.4 mg/s, 0.6 mg/s, 0.9 mg/s, 1.3 mg/s, 1.9 mg/s, or 2.5 mg/s.

Typically, the delivered aerosol has an inhalable aerosol particle density greater than $10^6$ particles/mL. More typically, the aerosol has an inhalable aerosol particle density greater than $10^7$ particles/mL, and most typically, the aerosol has an inhalable aerosol particle density greater than $10^8$ particles/mL.

Typically, where the aerosol comprises albuterol, the aerosol has an inhalable aerosol drug mass density of between 10 μg/L and 200 μg/L. More typically, the aerosol has an inhalable aerosol drug mass density of between 17.5 μg/L and 75 μg/L, and most typically, the aerosol has an inhalable aerosol drug mass density of between 25 μg/L and 50 μg/L.

Typically, where the aerosol comprises metaproterenol, the aerosol has an inhalable aerosol drug mass density of between 0.1 mg/L and 1.5 mg/L. More typically, the aerosol has an inhalable aerosol drug mass density of between 0.15 mg/L and 1.25 mg/L, and most typically, the aerosol has an inhalable aerosol drug mass density of between 0.2 mg/L and 1 mg/L.

Typically, where the aerosol comprises terbutaline, the aerosol has an inhalable aerosol drug mass density of between 0.01 mg/L and 1 mg/L. More typically, the aerosol has an inhalable aerosol drug mass density of between 0.03 mg/L and 0.75 mg/L. Most typically, the aerosol has an inhalable aerosol drug mass density of between 0.05 mg/L and 0.5 mg/L.

Typically, where the aerosol comprises tramcinolone acetonide, the aerosol has an inhalable aerosol drug mass density of between 10 μg/L and 200 μg/L. More typically, the aerosol has an inhalable aerosol drug mass density of between 20 μg/L and 175 μg/L. Most typically, the aerosol has an inhalable aerosol drug mass density of between 30 μg/L and 150 μg/L.

Delivery Device

The delivery devices described herein for administering a respiratory drug condensation aerosol typically comprise an element for heating the asthma drug composition to form a vapor, an element allowing the vapor to cool, thereby forming a condensation aerosol, and an element permitting a user to inhale the aerosol. The delivery device may be combined with a composition comprising a respiratory drug in unit dose form, for use as a kit.

One suitable device is illustrated in FIG. 1. Delivery device 100 has a proximal end 102 and a distal end 104, a solid support 106, a power source 108, and a mouthpiece 110. In this depiction, solid support 106 also comprises a heating module. An asthma drug composition is deposited on solid support 106. Upon activation of a user activated switch 114, power source 108 initiates heating of heating module (e.g, through ignition of combustible fuel or passage of current through a resistive heating element, etc.).

The respiratory drug composition vaporizes and condenses to form a condensation aerosol prior to reaching the mouthpiece 110 at the proximal end of the device 102. Air flow traveling from the device distal end 104 to the mouthpiece 110 carries the condensation aerosol to the mouthpiece 110, where it is inhaled by a user.

The devices described herein may additionally contain a variety of components to facilitate aerosol delivery. For instance, the device may include any component known in the art to control the timing of drug aerosolization relative to inhalation (e.g., breath-actuation). Similarly, the device may include a component to provide feedback to patients on the rate and/or volume of inhalation, or a component to prevent excessive use (i.e., "lock-out" feature). In addition, the device may further include a component to prevent use by unauthorized individuals, and a component to record dosing histories. These components may be used alone, or in combination with other components.

The element that allows cooling may be of any configuration. For example, it may be an inert passageway linking the heating means to the inhalation means. Similarly, the element permitting inhalation by a user may be of any configuration. For example, it may be an exit portal that forms a connection between the cooling element and the user's respiratory system.

Figure 2A:
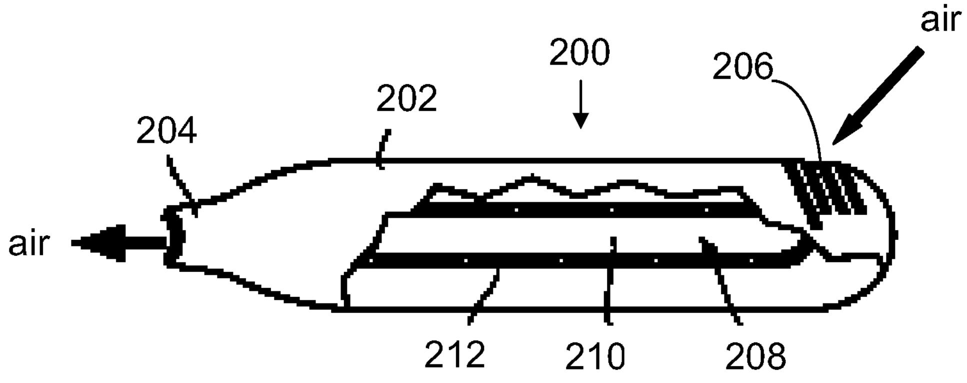
FIGS. 2A and 2B are illustrations of other exemplary devices that may be used to form and administer the aerosols described herein.
Figure 2B:
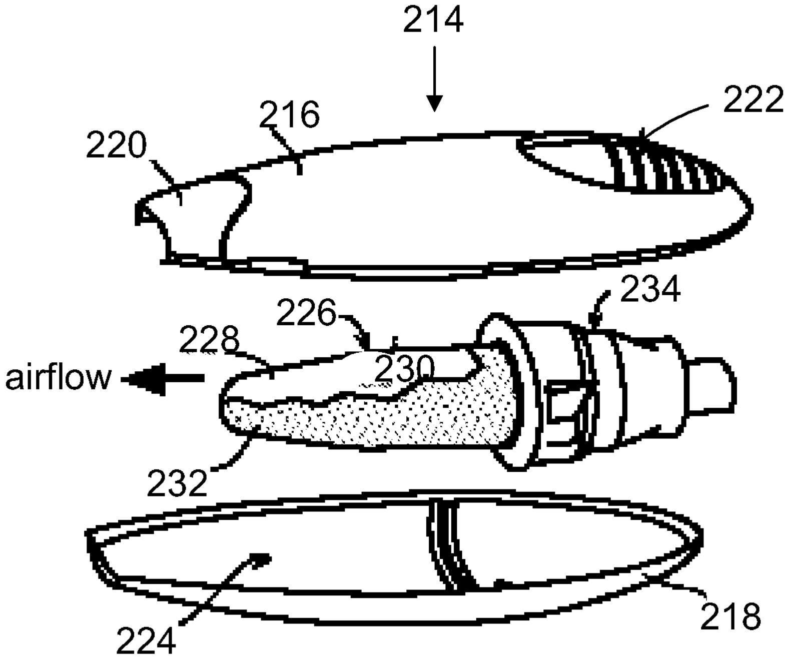

Other suitable devices for use with the aerosols described herein are shown in FIGS. 2A and 2B. As shown in FIG. 2A, there is a device 200 comprising an element for heating an asthma drug composition to form a vapor, an element allowing the vapor to cool, thereby forming a condensation aerosol, and an element permitting a user to inhale the aerosol. Device 200 also comprises a housing 202 with a tapered end 204 for insertion into the mouth of a user. On the end opposite tapered end 204, the housing has one or more openings, such as slots 206, for air intake when a user places the device in the mouth and inhales a breath. Within housing 202 is a solid support 208, visible in the cut-away portion of the figure. At least a portion of the solid support is coated on a surface 210 with a film 212 of an asthma drug composition.

Typically, the solid support 208 is heated to a temperature sufficient to vaporize all or a portion of the film 212, so that the respiratory drug composition forms a vapor that becomes entrained in a stream of air during inhalation. As noted above, heating of the solid support 208 may be accomplished using, for example, an electrically-resistive wire embedded or inserted into the substrate and connected to a battery disposed in the housing. The heating can be actuated, for example, with a button on the housing or via breath actuation, as is known in the art.

FIG. 2B shows another device that may be used to form and deliver the aerosols described herein. The device, 214 comprises an element for heating a respiratory drug composition to form a vapor, an element allowing the vapor to cool, thereby forming a condensation aerosol, and an element permitting a user to inhale the aerosol. The device also comprises an upper external housing member 216 and a lower external housing member 218 that fit together.

Shown in the depiction of FIG. 2B, the downstream end of each housing member is gently tapered for insertion into a user's mouth, as best seen on upper housing member 216 at downstream end 220. The upstream end of the upper and lower housing members are slotted, as seen best in the figure in the upper housing member at 222, to provide for air intake when a user inhales. The upper and lower housing members when fitted together define a chamber 224. Positioned within chamber 224 is a solid support 226, shown in a partial cutaway view.

As shown in FIG. 2B, the solid support shown there is of a substantially cylindrical configuration having a slight taper. However, as described above the solid support may be of any desirable configuration. At least a portion of the solid support surface 228 is coated with a respiratory drug composition film 230. Visible in the cutaway portion of the solid support is an interior region 232, which comprises a substance suitable to generate heat. The substance may be, for example, a solid chemical fuel, chemical reagents that mix exothermically, an electrically resistive wire, or the like. A power supply source, if needed for heating, and any necessary valving for the inhalation device may be contained in end piece 234.

The device may also include a gas-flow control valve disposed upstream of the solid support, for limiting gas-flow rate through the condensation region. The gas-flow valve may, for example, include an inlet port communicating with the chamber, and a deformable flap adapted to divert or restrict air flow away from the port increasingly, with increasing pressure drop across the valve. Similarly, the gas-flow valve may include an actuation switch. In this variation, the valve movement would be in response to an air pressure differential across the valve, which for example, could function to close the switch. The gas-flow valve may also include an orifice designed to limit airflow rate into the chamber.

The device may also include a bypass valve communicating with the chamber downstream of the unit for offsetting the decrease in airflow produced by the gas-flow control valve, as the user draws air into the chamber. In this way, the bypass valve could cooperate with the gas-control valve to control the flow through the condensation region of the chamber as well as the total amount of air being drawn through the device. Thus the total volumetric airflow through the device in this variation would be the sum of the volumetric airflow rate through the gas-control valve and the volumetric airflow rate through the bypass valve.

The gas control valve could, for example, function to limit air drawn into the device to a preselected level, e.g., 15 L/minute. In this way, air flow for producing particles of a desired size may be preselected and produced. For example, once this selected airflow level is reached, additional air drawn into the device would create a pressure drop across the bypass valve, which in turn would accommodate airflow through the bypass valve into the downstream end of the device adjacent the user's mouth. Thus, the user senses a full breath being drawn in, with the two valves distributing the total airflow between desired airflow rate and bypass airflow rate.

These valves may be used to control the gas velocity through the condensation region of the chamber and hence to control the particle size of the aerosol particles produced. Typically, the faster the airflow, the smaller the particles. Thus, to achieve smaller or larger particles, the gas velocity through the condensation region of the chamber may be altered by modifying the gas-flow control valve to increase or decrease the volumetric airflow rate. For example, to produce condensation particles in the size range of about 2-4 μm MMAD, a chamber having substantially smooth-surfaced walls would have a selected gas-flow rate in the range of 4-50 L/minute.

Additionally, as will be appreciated by one of skill in the art, particle size may be altered by modifying the cross-section of the chamber condensation region to increase or decrease linear gas velocity for a given volumetric flow rate, and/or the presence or absence of structures that produce turbulence within the chamber. Thus, for example to produce condensation particles in the size range 10-100 nm MMAD, the chamber may provide gas-flow barriers for creating air turbulence within the condensation chamber. These barriers are typically placed within a few thousands of an inch from the substrate surface. Particle size is discussed in more detail below.

Figure 3A:
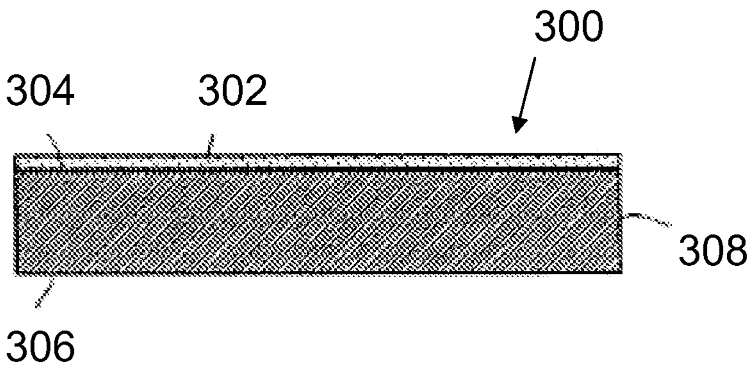
FIGS. 3A and 3B illustrate solid supports suitable for use with the devices and methods described herein.
Figure 3B:
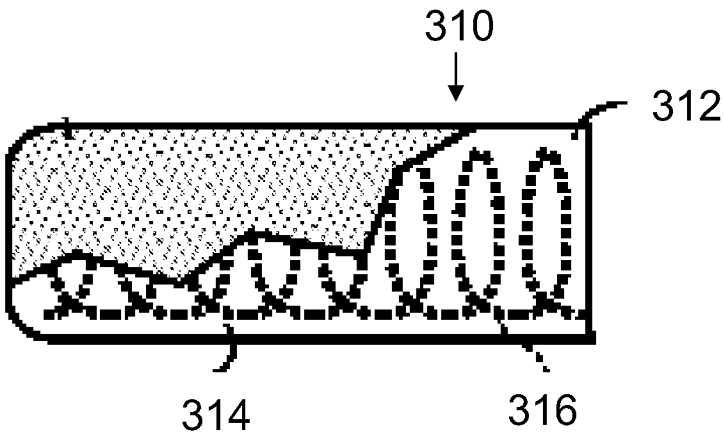

FIGS. 3A and 3B provide exploded views of solid supports that may be used in combination with the devices described herein. As shown in FIG. 3A, there is a solid support 300 having a respiratory drug composition coating 302 at least a portion of the upper surface 304. While the coating 302 is shown on upper surface 304 in FIG. 3A, it should be understood that it need not be so. Indeed, the coating may be placed on any suitable surface, such as surfaces 306 and 308.

FIG. 3B provides a perspective, cut-away view of another solid support 310 that may be used with the methods and devices herein described. As shown there, the solid support 310 comprises a cylindrically-shaped substrate 312. This substrate may be formed from a heat-conductive material, for example. The exterior surface 314 of substrate 312 is coated with an asthma drug composition. As shown in the cut-away portion, there is a heating element 316 disposed in the substrate. The substrate can be hollow with a heating element inserted into the hollow space or solid with a heating element incorporated into the substrate.

The illustrative heating element shown in FIG. 3B is shown as an electrical resistive wire that produces heat when a current flows through it, but as noted above, a number of different heating methods and corresponding devices are acceptable. For example, acceptable heat sources can supply heat to the solid support at rates that rapidly achieve a temperature sufficient to completely vaporize the asthma drug composition from the support surface. For example, heat sources that achieve a temperature of 200° C. to 500° C. within a period of 2 seconds, although it should be appreciated that the temperature chosen will be dependent upon the vaporization properties of the asthma drug composition.

Respiratory Drug Composition Film Thickness

Typically, the respiratory drug composition film coated on the solid support has a thickness of between about 0.05-20 μm, and typically a thickness between 0.1-15 μm. More typically, the thickness is between about 0.2-10 μm; even more typically, the thickness is between about 0.5-10 μm, and most typically, the thickness is between about 0.5-5 μm. The desirable film thickness for any given respiratory drug composition is typically determined by an iterative process in which the desired yield and purity of the condensation aerosol composition are selected or known.

For example, if the purity of the particles is less than that which is desired, or if the percent yield is less than that which is desired, the thickness of the drug film is adjusted to a thickness different from the initial film thickness. The purity and yield are then determined at the adjusted film thickness, and this process is repeated until the desired purity and yield are achieved. After selection of an appropriate film thickness, the area of substrate required to provide a therapeutically effective dose, is determined.

Solid Support Surface Area

As noted above, the surface area of the solid support is selected such that it is sufficient to yield a therapeutically effective dose. The amount of respiratory drug required to provide a therapeutically effective dose is generally known in the art, and is discussed in more detail below. The substrate area may then be determined using the following equation:

film thickness (cm) × drug density (g/cm3) ×
substrate area (cm2) = dose (g)
OR
substrate area (cm2) = dose (g)/[film thickness (cm) ×
drug density (g/cm3)]

The drug mass can be determined by weighing the substrate before and after formation of the drug film or by extracting the drug and measuring the amount analytically. Drug density can be determined experimentally by a variety of well known techniques, or may be found in the literature or in reference texts, such as in the CRC. An assumption of unit density is acceptable if an actual drug density is not known.

Dosage of Respiratory Drug Containing Aerosols

The dosage amount of respiratory drugs in aerosol form is generally less than the standard dose of the drug given orally. For instance, albuterol, metaproterenol, or terbutaline given at strengths of 2 mg to 4 mg, 10 mg to 20 mg, and 2.5 mg to 5 mg respectively for the treatment of asthma. As aerosols, 10 μg to 200 μg of albuterol, 0.1 mg to 1.5 mg metaproterenol, 0.01 mg to 1 mg terbutaline, and 10 μg to 200 μg of triamcinolone acetonide are generally provided per inhalation for the same indication.

A dosage of respiratory drug aerosol may be administered in a single inhalation or may be administered in more than one inhalation, such as a series of inhalations. Where the drug is administered as a series of inhalations, the inhalations are typically taken within an hour or less (dosage equals sum of inhaled amounts). When the drug is administered as a series of inhalations, a different amount may be delivered in each inhalation.

Typically, in the respiratory drug containing aerosol, between 0.005 mg and 10 mg of a respiratory drug is delivered to the mammal in a single inspiration. More typically, between 0.01 mg and 3 mg of a respiratory drug is delivered to the mammal in a single inspiration, and most typically, between 0.02 mg and 1.5 mg of a respiratory drug is delivered to the mammal in a single inspiration.

One can determine the appropriate dose of respiratory drug aerosol to treat a particular condition using methods such as animal experiments and a dose-finding (Phase I/II) clinical trial. Typically, studies are first conducted to determine dose limiting toxicity in a mammal. Initial dose levels for testing in humans are generally less than or equal to one-tenth of the dose on a body surface area basis that resulted in dose-limiting toxicity in the mammal. Dose escalation in humans is then performed, until either an optimal therapeutic response is obtained or a dose-limiting toxicity is encountered.

Particle Size

Efficient aerosol delivery to the lungs requires that the particles have certain penetration and settling or diffusional characteristics. Deposition in the small airways of the lungs may occur by either gravitational settling or diffusion, and can only occur if the delivered particles are able to pass from the mouth through the larynx to the airways and lungs. Avoiding impaction in the mouth and upper respiratory tract requires particles in the size range between about 10 nm and 5 µm, because particles much smaller than 10 nm (e.g., vapors) diffuse so rapidly that they are lost in the mouth and upper-most airways, and particles larger than 5 µm tend to inertially impact in the back of the throat and larynx. To avoid impaction, particles smaller than 4 µm or even 3 µm are preferred. Once in the airways, for the treatment of airway disease (e.g., asthma), particle sizes that either diffuse or settle due to gravity into the airway walls are preferred. This contrasts with treatment of alveolar disease or systemic disease (where alveolar absorption of drug into the blood is desirable), in that particle sizes that pass through the airways and settle or diffuse into the deepest-most lung tissues of the alveoli (e.g., 1-3 µm or 10 nm-100 nm particles) are preferred. Thus, for treatment of airway disease, when deposition by gravitational settling is desired, aerosols characterized by a mass median aerodynamic diameter (MMAD) in the about 1.5 µm to 4 µm size range are preferred, and aerosols with a 2 µm to 3 µm MMAD are more preferred. For treatment of airway disease, when deposition of particles by diffusion is desired, aerosols characterized by a mass median aerodynamic diameter (MMAD) in the about 10 nm to 300 nm size range are preferred, and aerosols with a 10 nm to 200 nm or 10 nm to 100 nm MMAD are more preferred. Typically, in order to produce particles having a desired MMAD, gas or air is passed over the solid support at a certain flow rate.

Typically, the higher the flow rate, the smaller the particles that are formed. Therefore, in order to achieve smaller or larger particles, the flow rate through the condensation region of the delivery device may be altered. This may be done, for example, by modifying a gas-flow control valve to increase or decrease the volumetric airflow rate. To illustrate, condensation particles in the size range 1.5-4 µm MMAD may be produced by selecting the gas-flow rate to be in a range of 4-50 L/minute.

Additionally, as will be appreciated by one of skill in the art, particle size may also be altered by modifying the cross-section of the chamber condensation region to increase or decrease linear gas velocity for a given volumetric flow rate. In addition, particle size may also be altered by the presence or absence of structures that produce turbulence within the chamber. Thus, for example to produce condensation particles in the size range 10-100 nm MMAD, the chamber may provide gas-flow barriers for creating air turbulence within the condensation chamber. These barriers are typically placed within a few thousands of an inch from the substrate surface.

Analysis of Respiratory Drug Aerosols

Purity of a respiratory drug aerosol may be determined using a number of different methods. Examples of suitable methods for determining aerosol purity are described in Sekine et al., *Journal of Forensic Science* 32:1271-1280 (1987) and in Martin et al., *Journal of Analytic Toxicology* 13:158-162 (1989).

One suitable method involves the use of a trap. In this method, the aerosol is collected in a trap in order to determine the percent or fraction of thermal degradation product. Any suitable trap may be used. Suitable traps include filters, glass wool, impingers, solvent traps, cold traps, and the like. Filters are often most desirable. The trap is then typically extracted with a solvent, e.g. acetonitrile, and the extract subjected to analysis by any of a variety of analytical methods known in the art, for example, gas, liquid, and high performance liquid chromatography particularly useful.

The gas or liquid chromatography method typically includes a detector system, such as a mass spectrometry detector or an ultraviolet absorption detector. Ideally, the detector system allows determination of the quantity of the components of the drug composition and of the byproduct, by weight. This is achieved in practice by measuring the signal obtained upon analysis of one or more known mass(es) of components of the drug composition or byproduct (standards) and then comparing the signal obtained upon analysis of the aerosol to that obtained upon analysis of the standard(s), an approach well known in the art.

In many cases, the structure of a thermal degradation product may not be known or a standard for it may not be available. In such cases, one may calculate the weight fraction of the thermal degradation product by assuming it has an identical response coefficient (e.g. for ultraviolet absorption detection, identical extinction coefficient) to the drug component or components in the respiratory drug composition. When conducting such analysis, thermal degradation products present in less than a very small fraction of the drug compound, e.g. less than 0.2% or 0.1% or 0.03% of the drug compound, are typically excluded. Because of the frequent necessity to assume an identical response coefficient between drug and byproduct in calculating a weight percentage of thermal degradation product, it is often more desirable to use an analytical approach in which such an assumption has a high probability of validity. In this respect, high performance liquid chromatography with detection by absorption of ultraviolet light at 225 nm is typically desirable. UV absorption at 250 nm may be used for detection of compounds in cases where the compound absorbs more strongly at 250 nm or for other reasons one skilled in the art would consider detection at 250 nm the most appropriate means of estimating purity by weight using HPLC analysis. In certain cases where analysis of the drug by UV are not viable, other analytical tools such as GC/MS or LC/MS may be used to determine purity.

It is possible that modifying the form of the drug may impact the purity of the aerosol obtained. Although not always the case, the free base or free acid form of the drug as opposed to the salt, generally results in either a higher purity or yield of the resultant aerosol. Therefore, in certain circumstances, it may be more desirable to use the free base or free acid forms of the compounds used. Similarly, it is possible that changing the gas under which vaporization of the composition occurs may also impact the purity.

Other Analytical Methods

Particle size distribution of a respiratory drug aerosol may be determined using any suitable method in the art (e.g., cascade impaction). An Andersen Eight Stage Non-viable Cascade Impactor (Andersen Instruments, Smyrna, Ga.) linked to a furnace tube by a mock throat (USP throat, Andersen Instruments, Smyrna, Ga.) is one system used for cascade impaction studies. For most pharmaceutical aerosol testing the Anderson Cascade Impactor (ACI) is a gold standard instrument. The ACI inertially separates the aerosol into 7 stages with progressively smaller cutoff diameters from 9.0 μm to 0.4 μm. However, when testing particle size distribution of aerosols that have a substantial fraction less than 1 μm aerodynamic diameter, or aerosols with a MMAD less than 1 micrometer, the ACI is does not provide optimal resolution at that size range. The ACI has only one stage with a cutoff diameter less than 1 μm, at 0.4 mm and thus cannot provide much information about the size distribution of an aerosol below 1 μm. A better alternative is the Micro Orifice Uniform Deposit Impactor (MOUDI) designed and distributed by MSP Corporation in Shoreview, Minn. The MOUDI model 110 has eleven stages, five with cutoff diameters less than 1.0 μm. The stage 0 cut diameter is 18 μm and below 1 μm the cutoffs are 0.56, 0.32, 0.18, 0.1, and 0.056 μm. If additional resolution is required below 0.056 μm, the nano-MOUDI model 115 provides cutoffs of 0.032, 0.018 and 0.010 μm. The performance of these devices has been documented by Virgil Marple, Kenneth Rubow, and Steven Behm (see Marple et al., Aerosol Science and Technology 14:434-446, 1991).

Inhalable aerosol drug mass density may be determined, for example, by delivering a drug-containing aerosol into a confined chamber via an inhalation device and measuring the amount of active drug compound collected in the chamber. Typically, the aerosol is drawn into the chamber by having a pressure gradient between the device and the chamber, wherein the chamber is at lower pressure than the device. The volume of the chamber should approximate the tidal volume of an inhaling patient. The amount of active drug compound collected in the chamber is determined by extracting the chamber, conducting chromatographic analysis of the extract and comparing the results of the chromatographic analysis to those of a standard containing known amounts of drug.

Inhalable aerosol particle density may be determined, for example, by delivering aerosol phase drug into a confined chamber via an inhalation device and measuring the number of particles of given size collected in the chamber. The number of particles of a given size may be directly measured based on the light-scattering properties of the particles. Alternatively, the number of particles of a given size may be determined by measuring the mass of particles within the given size range and calculating the number of particles based on the mass as follows: Total number of particles=Sum (from size range 1 to size range N) of number of particles in each size range. Number of particles in a given size range=Mass in the size range/Mass of a typical particle in the size range. Mass of a typical particle in a given size range=$\pi*D^3\phi/6$, where D is a typical particle diameter in the size range (generally, the mean boundary MMADs defining the size range) in microns, $\phi$ is the particle density (in g/mL) and mass is given in units of picograms ($g^{-12}$).

Rate of inhalable aerosol particle formation may be determined, for example, by delivering aerosol phase drug into a confined chamber via an inhalation device. The delivery is for a set period of time (e.g., 1 s), and the number of particles of a given size collected in the chamber is determined as outlined above. The rate of particle formation is equal to the number of 100 nm to 5 micron particles collected divided by the duration of the collection time.

Rate of aerosol formation may be determined, for example, by delivering aerosol phase drug into a confined chamber via an inhalation device. The delivery is for a set period of time (e.g., 1 s), and the mass of particulate matter collected is determined by weighing the confined chamber before and after the delivery of the particulate matter. The rate of aerosol formation is equal to the increase in mass in the chamber divided by the duration of the collection time. Alternatively, where a change in mass of the delivery device or component thereof can only occur through release of the aerosol phase particulate matter, the mass of particulate matter may be equated with the mass lost from the device or component during the delivery of the aerosol. In this case, the rate of aerosol formation is equal to the decrease in mass of the device or component during the delivery event divided by the duration of the delivery event.

Rate of drug aerosol formation may be determined, for example, by delivering an asthma drug aerosol into a confined chamber via an inhalation device over a set period of time (e.g., 1 s). Where the aerosol is pure asthma drug, the amount of drug collected in the chamber is measured as described above. The rate of drug aerosol formation is equal to the amount of asthma drug collected in the chamber divided by the duration of the collection time. Where the asthma drug aerosol comprises a pharmaceutically acceptable excipient, multiplying the rate of aerosol formation by the percentage of asthma drug in the aerosol provides the rate of drug aerosol formation.

General Procedure for Determining Whether a Respiratory Drug is a "Heat Stable Drug"

Drug is dissolved or suspended in a solvent (e.g., dichloromethane or methanol). The solution or suspension is coated to about a 4 micron thickness on a stainless steel substrate of about 8 $cm^2$ surface area. The substrate may either be a standard stainless steel foil or a heat-passivated stainless steel foil. The substrate is heated to a temperature sufficient to generate a thermal vapor (generally ~350° C.) but at least to a temperature of 200° C. with an air flow typically of 20 L/min (1 m/s) passing over the film during heating. The heating is done in a volatilization chamber fitted with a trap (such as described in the Examples above). After vaporization is complete, airflow is discontinued and the resultant aerosol is analyzed for purity using the methods disclosed herein. If the resultant aerosol contains less than 10% drug degradation product, i.e., the TSR≧9, then the drug is a heat stable drug. If, however, at about 4 micron thickness, greater than 10% degradation is determined, the experiment is repeated at the same conditions, except that film thicknesses of about 1.5 microns, and of about 0.5 micron, respectively, are used. If a decrease in degradation products relative to the 4 micron thickness is seen at either of these thinner film thicknesses, a plot of film thickness versus purity is graphed and extrapolated out to a film thickness of 0.05 microns. The graph is used to determine if there exists a film thickness where the purity of the aerosol would be such that it contains less than 10% drug degradation products. If such a point exists on the graph, then the drug is defined as a heat stable drug.

Methods of Treating Respiratory Ailments

Also described herein are methods for treating a respiratory ailment. Typically the methods comprise the step of administering a therapeutically effective amount of a respiratory drug condensation aerosol to a person with a respiratory ailment. Typically the step of administering the respiratory drug condensation aerosol comprises the step of administering an orally inhalable respiratory drug condensation aerosol to the person with the respiratory ailment.

The respiratory drug aerosol may be administered in a single inhalation, or in more than one inhalation, as described above. The respiratory drug condensation aerosol may comprise a respiratory drug composition as described above. The respiratory drug composition typically comprises at least one respiratory drug selected from the group consisting of β-adrenergics, methyl xanthines, anti-cholinergics, corticosteroids, mediator-release inhibitors, anti-leukotriene drugs, asthma inhibitors, asthma antagonists, and pharmaceutically acceptable analogs, derivatives, and mixtures thereof. In some variations, the asthma drug condensation aerosol has a MMAD in the range of about 2-4 μm.

In some variations, the method for treating a respiratory ailment comprises the step of administering a therapeutically effective amount of a respiratory drug aerosol to a person with the respiratory ailment, wherein the respiratory drug aerosol comprises a respiratory drug and has a MMAD in the range of about 2-4 μm, and wherein the aerosol has a purity of greater than 90%.

WORKING EXAMPLES

The following working examples are meant to be illustrative, and are in no way intended to limit the scope of the invention. Albuterol, metaproterenol hemisulfate, terbutaline sulfate, and triamcinolone acetonide are commercially available from Sigma-Aldrich.

Preparation of Drug-Coating Solution

Drug was dissolved in an appropriate solvent. Common solvent choices included methanol, dichlorometane, methyl ethyl ketone, diethyl ether, 3:1 chloroform:methanol mixture, 1:1 dichlorormethane:methyl ethyl ketone mixture, dimethylformamide, and deionized water. Sonication and/or heat were used as necessary to dissolve the compound. The drug concentration was typically between 50-200 mg/mL.

Volatilization Using Stainless Steel Foil

Strips of clean 304 stainless steel foil (0.0125 cm thick, Thin Metal Sales) having dimensions 1.3 cm by 7.0 cm were dip-coated approximately 4.5 to 5 cm on the strip with an asthma drug solution prepared as described above. The foil was then partially dipped three times into solvent to rinse drug off of the last 2-3 cm of the dipped end of the foil. Alternatively, the drug-coating from this bottom 2-3 cm area was carefully taken off with a razor blade. The final coated area was between 2.0-2.5 cm by 1.3 cm on both sides of the foil, for a total area of between 5.2-6.5 $cm^2$. Foils were prepared as stated above and then some were extracted with methanol or acetonitrile as standards. The amount of drug was determined from quantitative HPLC analysis. Using the known drug-coated surface area, the thickness was then calculated.

After drying, the drug-coated foil was placed into a volatilization chamber constructed of a Delrin block (the airway) and brass bars, which served as electrodes. The dimensions of the airway were 1.3 cm high by 2.6 cm wide by 8.9 cm long. The drug-coated foil was placed into the volatilization chamber such that the drug-coated section was between the two sets of electrodes. After securing the top of the volatilization chamber, the electrodes were connected to a 1 Farad capacitor (Phoenix Gold). The back of the volatilization chamber was connected to a two micron Teflon® filter (Savillex) and filter housing, which were in turn connected to the house vacuum. Sufficient airflow was initiated (typically 30 L/min=1.5 m/sec), at which point the capacitor was charged with a power supply, typically to between 14-17 Volts.

The circuit was closed with a switch, causing the drug-coated foil to resistively heat to temperatures of about 280-430° C. (as measured with an infrared camera (FLIR Thermacam SC3000)), in about 200 milliseconds. After the drug had vaporized, airflow was stopped and the Teflon® filter was extracted with acetonitrile. Drug extracted from the filter was analyzed generally by HPLC UV absorbance generally at 225 nm using a gradient method aimed at detection of impurities to determine percent purity. Also, the extracted drug was quantified to determine a percent yield, based on the mass of drug initially coated onto the substrate. A percent recovery was determined by quantifying any drug remaining on the substrate and chamber walls, adding this to the quantity of drug recovered in the filter and comparing it to the mass of drug initially coated onto the substrate.

Volatilization Using Aluminum Foil and Halogen Bulb

A substrate of aluminum foil (3.5 cm×7 cm; 0.0005 inches thick) was precleaned with acetone. A solution of drug in a minimal amount of solvent was coated onto the foil substrate. The solvent was allowed to evaporate. The coated foil was wrapped around a 300 watt halogen tube (Felt Electric Company, Pico Rivera, Calif.), which was inserted into a T-shaped glass tube sealed at two ends with parafilm. The parafilm was punctured with ten to fifteen needles for air flow. The third opening was connected to a 1 liter, 3-neck glass flask. The glass flask was further connected to a piston capable of drawing 1.1 liters of air through the flask. Ninety volts of alternating current (driven by line power controlled by a Variac) was run through the bulb for 6-7 seconds to generate a thermal vapor (including aerosol) which was drawn into the 1 liter flask. The aerosol was allowed to sediment onto the walls of the 1 liter flask for 30 minutes. The material collected on the flask walls was recovered and the following determinations were made: (1) the amount emitted, (2) the percent emitted, and (3) the purity of the aerosol by reverse-phase HPLC analysis with detection by typically by absorption of 225 nm light. Additionally, any material remaining on the substrate was collected and quantified.

Volatilization Using Stainless Steel Cylinder

A hollow stainless steel cylinder with thin walls, typically 0.12 mm wall thickness, a diameter of 13 mm, and a length of 34 mm was cleaned in dichloromethane, methanol, and acetone, then dried, and fired at least once to remove any residual volatile material and to thermally passivate the stainless steel surface. The substrate was then dip-coated with a drug coating solution (prepared as described above). The dip-coating was done using a computerized dipcoating machine to produce a thin layer of drug on the outside of the substrate surface. The substrate was lowered into the drug solution and then removed from the solvent at a rate of typically 5-25 cm/sec. (To coat larger amounts of material on the substrate, the substrate was removed more rapidly from the solvent or the solution used was more concentrated.) The substrate was then allowed to dry for 30 minutes inside a fume hood. If either dimethylformamide (DMF) or a water mixture was used as a dip-coating solvent, the substrate was vacuum dried inside a desiccator for a minimum of one hour. The drug-coated portion of the cylinder generally has a surface area of 8 $cm^2$. By assuming a unit density for the drug, the initial drug coating thickness was calculated. The amount of drug coated onto the substrates was determined in the same manner as that described above: the substrates were coated, then extracted with methanol or acetonitrile and analyzed with quantitative HPLC methods, to determine the mass of drug coated onto the substrate.

The drug-coated substrate was placed in a surrounding glass tube connected at the exit end via Tygon® tubing to a filter holder fitted with a Teflon® filter (Savillex). The junction of the tubing and the filter was sealed with paraffin film. The substrate was placed in a fitting for connection to two 1 Farad capacitors wired in parallel and controlled by a high current relay. The capacitors were charged by a separate power source to about 18-22 Volts and most of the power was channeled to the substrate by closing a switch and allowing the capacitors to discharge into the substrate. The substrate was heated to a temperature of between about 300-500° C. in about 100 milliseconds. The heating process was done under an airflow of 15 L/min, which swept the vaporized drug aerosol into a 2 micron Teflon® filter.

After volatilization, the aerosol captured on the filter was recovered for quantification and analysis. The quantity of material recovered in the filter was used to determine a percent yield, based on the mass of drug coated onto the substrate. The material recovered in the filter was also analyzed generally by HPLC UV absorbance at typically 225 nm using a gradient method aimed at detection of impurities, to determine purity of the thermal vapor. Any material deposited on the glass sleeve or remaining on the substrate was also recovered and quantified to determine a percent total recovery ((mass of drug in filter+mass of drug remaining on substrate and glass sleeve)/mass of drug coated onto substrate). For compounds without UV absorption GCMS or LC/MS was used to determine purity and to quantify the recovery. Some samples were further analyzed by LC/MS to confirm the molecular weight of the drug and any degradants.

Example 1A

Volatilization of Albuterol

About 1.2 mg of albuterol was dip coated onto the stainless steel surface of a flashbar apparatus. (The flashbar is a cylinder 3.5 cm long and 1.3 cm in diameter consisting of a hollow tube of 0.005" thick stainless steel). Brass electrodes were connected to either end of the steel cylinder. The coated flashbar was secured in an electrical mount, which connected to two 1.0 Farad capacitors in parallel. An airway was provided by a 2 cm diameter glass sleeve placed around the flashbar. 15 L/min of room air were pulled by a house vacuum through the vaporization chamber and a filter housing, which contained a two-micron Teflon filter. A power supply charged the capacitors to 20.5 volts, at which point the circuit was closed with a switch and the stainless steel flashbar was resistively heated to about 400° C. within about 200 milliseconds. The drug aerosolized and flowed through the airway and into the filter. The Teflon filter was extracted with 5 mL of acetonitrile, and the sample was run through an HPLC for purity analysis. Purity analysis indicated that the aerosol was 94.4% albuterol.

To obtain higher purity aerosols, one can coat a lesser amount of drug, yielding a thinner film to heat. A linear decrease in film thickness is associated with a linear decrease in impurities.

Example 1B

Volatilization of Albuterol

Figure 4:
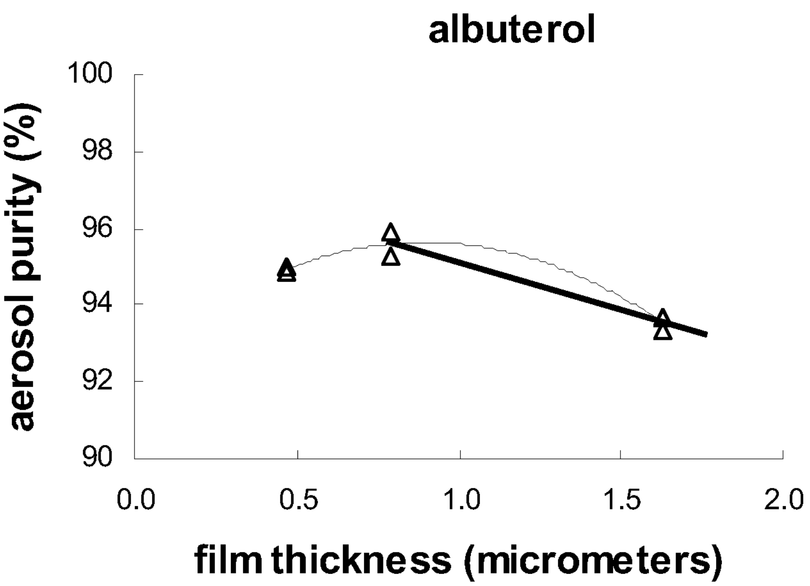
FIG. 4 is a plot depicting the effects of film thickness on aerosol purity for albuterol.

Albuterol (MW 239, melting point 158° C., MDI inhalation dose 0.18 mg), a bronchodilator, was coated onto six stainless steel foil substrates (5 $cm^2$) according to the method “Volatilization Using Stainless Steel Foil” described above. The calculated thickness of the drug film on each substrate ranged from about 0.4 μm to about 1.6 μm. The substrates were heated as described above by charging the capacitors to 15 V. Purity of the drug aerosol particles from each substrate was determined and the results are shown in FIG. 4.

Example 2

Volatilization of Ephedrine

About 8.0 mg was coated onto an aluminum foil substrate as described above in “Volatilization Using Aluminum Foil and Halogen Bulb,” for a calculated drug film thickness of about 4.0 μm. The substrate was heated as described above. The purity of the drug-aerosol particles was determined to be about 99%.

Example 3

Volatilization of Metaproterenol

About 1.35 mg of metaproterenol was dip coated onto the stainless steel surface of a flashbar apparatus. (The flashbar is a cylinder 3.5 cm long and 1.3 cm in diameter consisting of a hollow tube of 0.005" thick stainless steel). Brass electrodes were connected to either end of the steel cylinder. The coated flashbar was secured in an electrical mount, which connected to two 1.0 Farad capacitors in parallel. An airway was provided by a 2 cm diameter glass sleeve placed around the flashbar. 15 L/min of room air were pulled by a house vacuum through the vaporization chamber and a filter housing, which contained a two-micron Teflon filter. A power supply charged the capacitors to 20.5 volts, at which point the circuit was closed with a switch and the stainless steel flashbar was resistively heated in the range of about 380-420° C. within about 200 milliseconds. The drug aerosolized and flowed through the airway and into the filter. The Teflon filter was extracted with 5 mL of acetonitrile, and the sample was run through an HPLC for purity analysis. Purity analysis indicated that the aerosol was 99.1% metaproterenol. A total mass of 1.2 mg was recovered from the test apparatus and substrate, for a total recovery of 88.9%.

Example 4

Volatilization of Terbutaline

About 2.32 mg of terbutaline was dip coated onto the stainless steel surface of a flashbar apparatus. (The flashbar is a cylinder 3.5 cm long and 1.3 cm in diameter consisting of a hollow tube of 0.005" thick stainless steel). Brass electrodes were connected to either end of the steel cylinder. The coated flashbar was secured in an electrical mount, which connected to two 1.0 Farad capacitors in parallel. An airway was provided by a 2 cm diameter glass sleeve placed around the flashbar. 15 L/min of room air were pulled by a house vacuum through the vaporization chamber and a filter housing, which contained a two-micron Teflon filter. A power supply charged the capacitors to 20.5 volts, at which point the circuit was closed with a switch and the stainless steel flashbar was resistively heated to about 400° C. within about 200 milliseconds. The drug aerosolized and flowed through the airway and into the filter. The Teflon filter was extracted with 5 mL of acetonitrile, and the sample was run through an HPLC for purity analysis. Purity analysis indicated that the aerosol was 99.3% terbutaline. A total mass of 1.9 mg was recovered from the test apparatus and substrate, for a total recovery of 83.5%.

Example 5

Volatilization of Budesonide

About 1.46 mg of budesonide was dip coated onto the stainless steel surface of a flashbar apparatus. (The flashbar is a cylinder 3.5 cm long and 1.3 cm in diameter consisting of a hollow tube of 0.005" thick stainless steel). Brass electrodes were connected to either end of the steel cylinder. The coated flashbar was secured in an electrical mount, which connected to two 1.0 Farad capacitors in parallel. An airway was provided by a 2 cm diameter glass sleeve placed around the flashbar. 15 L/min of room air were pulled by a house vacuum through the vaporization chamber and a filter housing, which contained a two-micron Teflon filter. A power supply charged the capacitors to 20.5 volts, at which point the circuit was closed with a switch and the stainless steel flashbar was resistively heated to about 400° C. within about 200 milliseconds. The drug aerosolized and flowed through the airway and into the filter. The Teflon filter was extracted with 5 mL of acetonitrile, and the sample was run through an HPLC for purity analysis. Purity analysis indicated that the aerosol was 70.5% budesonide. A total mass of 0.6 mg was recovered from the test apparatus and substrate, for a total recovery of 41.2%.

Example 6A

Volatilization of Ciclesonide

About 0.204 mg ciclesonide (MW 541, melting point 206.5-207° C., MDI inhalation dose 0.2 mg) was coated onto a stainless steel foil substrate (5 $cm^2$) according to the method "Volatilization Using Stainless Steel Foil" described above. The calculated thickness of the drug film was about 0.4 μm. The substrate was heated as described above by charging the capacitor to 15 V. Purity analysis indicated that the aerosol was 99.03% ciclesonide. A total mass of 0.2 mg was recovered from the test apparatus and substrate, for a total recovery of 100%.

Example 6B

Volatilization of Ciclesonide

Figure 5:
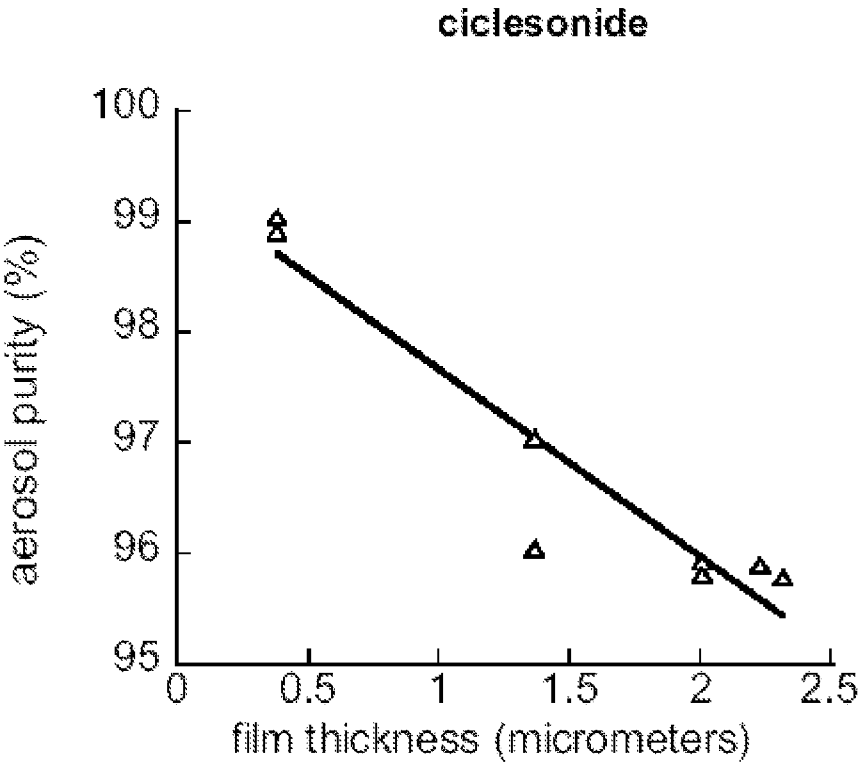
FIG. 5 is a plot depicting the effects of film thickness on aerosol purity for ciclesonide.

Ciclesonide (MW 541, melting point 206.5-207° C., oral dose 0.2 mg) was coated on stainless steel foil substrates (6 $cm^2$) according to the method "Volatilization Using Stainless Steel Foil" described above. Eight substrates were prepared, with the drug film thickness ranging from about 0.4 μm to about 2.4 μm. The substrates were heated as described above, with the capacitors charged with 15.0 or 15.5 V. Purity of the drug-aerosol particles from each substrate was determined and the results are shown in FIG. 5.

Example 7A

Volatilization of Flunisolide

About 0.3 mg flunisolide (MW 435, MDI inhalation dose 0.25 mg) was coated onto a stainless steel foil substrate (5 $cm^2$) according to the method "Volatilization Using Stainless Steel Foil" described above. The calculated thickness of the drug film was about 0.6 μm. The substrate was heated as described above by charging the capacitor to 15 V. Purity analysis indicated that the aerosol was 94.9% flunisolide. A total mass of 0.3 mg was recovered from the test apparatus and substrate, for a total recovery of 100%.

Example 7B

Volatilization of Flunisolide

About 0.5 mg of flunisolide was dip coated onto the stainless steel surface of a flashbar apparatus. (The flashbar is a cylinder 3.5 cm long and 1.3 cm in diameter consisting of a hollow tube of 0.005" thick stainless steel). Brass electrodes were connected to either end of the steel cylinder. The coated flashbar was secured in an electrical mount, which connected to two 1.0 Farad capacitors in parallel. An airway was provided by a 2 cm diameter glass sleeve placed around the flashbar. 15 L/min of room air were pulled by a house vacuum through the vaporization chamber and a filter housing, which contained a two-micron Teflon filter. A power supply charged the capacitors to 20.5 volts, at which point the circuit was closed with a switch and the stainless steel flashbar was resistively heated to about 400° C. within about 200 milliseconds. The drug aerosolized and flowed through the airway and into the filter. The Teflon filter was extracted with 5 mL of acetonitrile, and the sample was run through an HPLC for purity analysis. Purity analysis indicated that the aerosol was 97.6% flunisolide. A total mass of 0.5 mg was recovered from the test apparatus and substrate, for a total recovery of 100%.

Example 8

Volatilization of Fluticasone Propionate

About 0.3 mg fluticasone propionate (MW 501, MDI inhalation dose 0.044 mg) was coated onto a stainless steel foil substrate (5 $cm^2$) according to the method "Volatilization Using Stainless Steel Foil" described above. The calculated thickness of the drug film was about 0.6 μm. The substrate was heated as described above by charging the capacitor to 15 V. Purity analysis indicated that the aerosol was 91.6% fluticasone propionate. A total mass of about 0.2 mg was recovered from the test apparatus and substrate, for a total recovery of about 71.4%.

Example 9

Volatilization of Triamcinolone Acetonide

About 0.2 mg of triamcinolone acetonide was dip coated onto the stainless steel surface of a flashbar apparatus. (The flashbar is a cylinder 3.5 cm long and 1.3 cm in diameter consisting of a hollow tube of 0.005" thick stainless steel). Brass electrodes were connected to either end of the steel cylinder. The coated flashbar was secured in an electrical mount, which connected to two 1.0 Farad capacitors in parallel. An airway was provided by a 2 cm diameter glass sleeve placed around the flashbar. 15 L/min of room air were pulled by a house vacuum through the vaporization chamber and a filter housing, which contained a two-micron Teflon filter. A power supply charged the capacitors to 20.5 volts, at which point the circuit was closed with a switch and the stainless steel flashbar was resistively heated to about 400° C. within about 200 milliseconds. The drug aerosolized and flowed through the airway and into the filter. The Teflon filter was extracted with 5 mL of acetonitrile, and the sample was run through an HPLC for purity analysis. Purity analysis indicated that the aerosol was about 92.0% triamcinolone acetonide. A total mass of about 0.1 mg was recovered from the test apparatus and substrate, for a total recovery of about 50%.

Example 10

Volatilization of Theophylline

About 0.86 mg of theophylline was dip coated onto the stainless steel surface of a flashbar apparatus. (The flashbar is a cylinder 3.5 cm long and 1.3 cm in diameter consisting of a hollow tube of 0.005" thick stainless steel). Brass electrodes were connected to either end of the steel cylinder. The coated flashbar was secured in an electrical mount, which connected to two 1.0 Farad capacitors in parallel. An airway was provided by a 2 cm diameter glass sleeve placed around the flashbar. 15 L/min of room air were pulled by a house vacuum through the vaporization chamber and a filter housing, which contained a two-micron Teflon filter. A power supply charged the capacitors to 20.5 volts, at which point the circuit was closed with a switch and the stainless steel flashbar was resistively heated to about 400° C. within about 200 milliseconds. The drug aerosolized and flowed through the airway and into the filter. The Teflon filter was extracted with 5 mL of acetonitrile, and the sample was run through an HPLC for purity analysis. Purity analysis indicated that the aerosol was about 99.5% theophylline. A total mass of about 0.86 mg was recovered from the test apparatus and substrate, for a total recovery of about 100%.

Example 11

Volatilization of CPX

About 0.64 mg CPX (MW 304) was coated onto a stainless steel foil substrate (5 $cm^2$) according to the method "Volatilization Using Stainless Steel Foil" described above. The calculated thickness of the drug film was about 1.1 μm. The substrate was heated as described above by charging the capacitor to 15 V. Purity analysis indicated that the aerosol was 99.8% CPX. A total mass of about 0.6 mg was recovered from the test apparatus and substrate, for a total recovery of about 98.0%.

Example 12

Volatilization of IBMX

About 0.66 mg IBMX (MW 222) was coated onto a stainless steel foil substrate (5 $cm^2$) according to the method "Volatilization Using Stainless Steel Foil" described above. The calculated thickness of the drug film was about 1.2 μm. The substrate was heated as described above by charging the capacitor to 15 V. Purity analysis indicated that the aerosol was 99.9% IBMX. A total mass of about 0.66 mg was recovered from the test apparatus and substrate, for a total recovery of about 100%.

Example 13

Volatilization of a Mixture of Albuterol and Flunisolide

A solution of about 0.20 mg flunisolide (MW 435, oral dose 0.25 mg) and about 0.16 mg albuterol (MW 239, melting point 158° C., oral dose 0.18 mg) was coated onto a stainless steel foil substrate (5 $cm^2$) according to the method "Volatilization Using Stainless Steel Foil" described above. The calculated thickness of the drug film was about 0.64 μm. The substrate was heated as described above by charging the capacitor to 15.5 V. Purity analysis indicated that the aerosol was composed of albuterol (97.2% purity) and flunisolide (94.5%) along with their associated impurities. A total mass of 0.36 mg was recovered from the test apparatus and substrate, for a total recovery of 100%.

While the present invention has been described with reference to one or more particular variations, those skilled in the art will recognize that many changes may be made hereto without departing from the spirit and scope of the devices and methods herein described and claimed.

What we claim is:

1. A method of forming a drug containing aerosol comprising:

(a) heating a composition containing the drug and a pharmaceutically acceptable excipient coated on a solid support to form a vapor; and (b) condensing the vapor to form a condensation aerosol comprising particles, wherein the respiratory drug is selected from the group consisting of albuterol, epinephrine, metaproterenol, terbutaline, pseudoephedrine hydrochloride, bambuterol, bitolterol, carbuterol, clenbuterol, clorprenalin, dioxethedrine, eprozinol, etefedrine, ethylnorepinephrine, fenoterol, fenspiride, hexoprenaline, isoetharine, isoproterenol, mabuterol, methoxyphenamine, pirbuterol, procaterol, protokylol, rimiterol, salmeterol, soterenol, tretoquinol, tulobuterol, caffeine, theophylline, aminophylline, acefylline, bamifylline, doxofylline, dyphylline, etamiphyllin, etofylline, proxyphylline, reproterol, theobromine-1-acetic acid, atropine, ipratropium bromide, flutropium bromide, oxitropium bromide, tiotropium bromide, budesonide, beclomethasone, ciclesonide, dexamethasone, flunisolide, fluticasone propionate, triamcinolone acetonide, prednisolone, methylprednisolone, hydrocortisone, cromolyn sodium, nedocromil sodium, montelukast, zafirlukast, pirfenidone, CPX, IBMX, cilomilast, roflumilast, pumafentrine, domitroban, israpafant, ramatroban, seratrodast, tiaramide, zileuton, ambrisentan, bosentan, enrasentan, sitaxsentan, tezosentan, iloprost, treprostinil, and pharmaceutically acceptable analogs, wherein the particles comprise at least 10 percent by weight of the drug and less than 5 percent by weight of the drug degradation products, and the condensation aerosol has an MMAD of less than 5 microns.

2. The method according to claim 1, wherein the condensation aerosol has an MMAD of 0.01 to 3 microns.

3. The method according to claim 2, wherein the coated composition comprises at least 10 percent by weight of the drug.

4. The method according to claim 1, wherein the condensing comprises allowing the vapor to cool.

5. A method of forming a drug containing aerosol comprising:

(a) heating a composition containing a salt form of the drug coated on a solid support to form a vapor; and (b) condensing the vapor to form a condensation aerosol comprising particles, wherein the drug is selected from the group consisting of albuterol, epinephrine, metaproterenol, terbutaline, pseudoephedrine hydrochloride, bambuterol, bitolterol, carbuterol, clenbuterol, clorprenalin, dioxethedrine, eprozinol, etefedrine, ethylnorepinephrine, fenoterol, fenspiride, hexoprenaline, isoetharine, isoproterenol, mabuterol, methoxyphenamine, pirbuterol, procaterol, protokylol, rimiterol, salmeterol, soterenol, tretoquinol, tulobuterol, caffeine, theophylline, aminophylline, acefylline, bamifylline, doxofylline, dyphylline, etamiphyllin, etofylline, proxyphylline, reproterol, theobromine-1-acetic acid, atropine, ipratropium bromide, flutropium bromide, oxitropium bromide, tiotropium bromide, budesonide, beclomethasone, ciclesonide, dexamethasone, flunisolide, fluticasone propionate, triamcinolone acetonide, prednisolone, methylprednisolone, hydrocortisone, cromolyn sodium, nedocromil sodium, montelukast, zafirlukast, pirfenidone, CPX, IBMX, cilomilast, roflumilast, pumafentrine, domitroban, israpafant, ramatroban, seratrodast, tiaramide, zileuton, ambrisentan, bosentan, enrasentan, sitaxsentan, tezosentan, iloprost, treprostinil, and pharmaceutically acceptable analogs, derivatives, and mixtures thereof, and wherein the particles comprise at least 10 percent by weight of the drug and less than 5 percent by weight of the drug degradation products, and the condensation aerosol has an MMAD of less than 5 microns.

6. The method according to claim 5, wherein the condensation aerosol has an MMAD of 0.01 to 3 microns.

7. The method according to claim 6, wherein the coated composition comprises at least 10 percent by weight of the salt form of the drug.

8. The method according to claim 5, wherein the condensing comprises allowing the vapor to cool.

9. A method of forming a drug containing aerosol comprising:

(a) heating a composition containing the drug coated on a solid support to form a vapor, and (b) condensing the vapor to form a condensation aerosol comprising particles, wherein the drug is selected from the group consisting of albuterol, epinephrine, metaproterenol, terbutaline, pseudoephedrine hydrochloride, bambuterol, bitolterol, carbuterol, clenbuterol, clorprenalin, dioxethedrine, eprozinol, etefedrine, ethylnorepinephrine, fenoterol, fenspiride, hexoprenaline, isoetharine, isoproterenol, mabuterol, methoxyphenamine, pirbuterol, procaterol, protokylol, rimiterol, salmeterol, soterenol, tretoquinol, tulobuterol, caffeine, theophylline, aminophylline, acefylline, bamifylline, doxofylline, dyphylline, etamiphyllin, etofylline, proxyphylline, reproterol, theobromine-1-acetic acid, atropine, ipratropium bromide, flutropium bromide, oxitropium bromide, tiotropium bromide, budesonide, beclomethasone, ciclesonide, dexamethasone, flunisolide, fluticasone propionate, triamcinolone acetonide, prednisolone, methylprednisolone, hydrocortisone, cromolyn sodium, nedocromil sodium, montelukast, zafirlukast, pirfenidone, CPX, IBMX, cilomilast, roflumilast, pumafentrine, domitroban, israpafant, ramatroban, seratrodast, tiaramide, zileuton, ambrisentan, bosentan, enrasentan, sitaxsentan, tezosentan, iloprost, treprostinil, and pharmaceutically acceptable analogs, derivatives, and mixtures thereof, wherein the condensation aerosol is formed at a rate greater than 0.5 mg/second, and wherein the particles comprise at least 10 percent by weight of the drug and less than 5 percent by weight of the drug degradation products, and the condensation aerosol has an MMAD of less than 5 microns.

10. The method according to claim 9, wherein the condensation aerosol has an MMAD of 0.01 to 3 microns.

11. The method according to claim 10, wherein the condensation aerosol is formed at a rate greater than 0.75 mg/second.

12. The method according to claim 11, wherein the condensation aerosol is formed at a rate greater than 1 mg/second.

13. The method according to claim 12, wherein the condensation aerosol is formed at a rate greater than 2 mg/second.

14. The method according to claim 9, wherein the condensing comprises allowing the vapor to cool.

* * * * *